US006837615B2

(12) United States Patent
Newman

(10) Patent No.: US 6,837,615 B2
(45) Date of Patent: Jan. 4, 2005

(54) METHOD OF EVALUATING LEVEL OF ANXIETY OF PERSON BASED ON SKIN TEMPERATURE

(76) Inventor: John Scott Newman, 2151 N. Quebec St., Arlington, VA (US) 22207-3928

( * ) Notice: Subject to any disclaimer, the term of this patent is extended or adjusted under 35 U.S.C. 154(b) by 0 days.

(21) Appl. No.: 10/355,189

(22) Filed: Jan. 31, 2003

(65) Prior Publication Data

US 2003/0179807 A1 Sep. 25, 2003

Related U.S. Application Data

(60) Provisional application No. 60/365,189, filed on Mar. 19, 2002.

(51) Int. Cl.$^7$ .............................. G01N 25/00; G01J 5/00
(52) U.S. Cl. ........................................ 374/45; 374/121
(58) Field of Search ................... 374/45, 121; 600/474, 600/549

(56) References Cited

U.S. PATENT DOCUMENTS

| 4,538,617 | A |   | 9/1985 | Jensen |
| 4,608,990 | A |   | 9/1986 | Elings |
| 4,859,078 | A |   | 8/1989 | Bowman et al. |
| 5,507,291 | A |   | 4/1996 | Stirbl et al. |
| 5,771,261 | A |   | 6/1998 | Anbar |
| 2002/0044674 | A1 |   | 4/2002 | Pavlidis |
| 2003/0016726 | A1 | * | 1/2003 | Pavlidis ...................... 374/45 |
| 2003/0120140 | A1 | * | 6/2003 | Bango ......................... 600/407 |
| 2003/0133597 | A1 | * | 7/2003 | Moore et al. ............... 382/115 |

FOREIGN PATENT DOCUMENTS

| EP | 0 441 193 A1 | 8/1991 |   |
| EP | 0 441 193 B1 | 8/1991 |   |
| GB | 2 203 835 A  | 10/1988 |   |
| JP | 59195134 A | * 11/1984 | ............. G01J/5/48 |
| WO | WO 9808431 A1 | * 3/1998 | ............. A61B/5/00 |

OTHER PUBLICATIONS

Pavlidis, I., et al., "Thermal Facial Screening for Deception Detection", 2 pages, date unknown.
Pavlidis, I., et al., "Thermal Imaging for Anxiety Detection", Jun. 16, 2000, 6 pages.
Levine, J.A., et al., "The face of fear", *The Lancet*, vol. 357, No. 9270, Jun. 2, 2001, 2 pages.
Pavlidis, I., et al., "Thermal Image Analysis for Anxiety Detection", Oct. 7–10, 2001, 4 pages.
Pavlidis, I., et al., "Monitoring of Periorbital Blood Flow Rate Through Thermal Image Analysis and Its Application to Polygraph Testing", Proceedings 23$^{rd}$ Annual International Conference of the IEEE Engineering in Medicine and Biology Society, Istanbul, Turkey, Oct. 25–28, 2001, 5 pages.
Pearson, H., "Liars caught red–faced", *Nature*, Jan. 3, 2002, 2 pages.

(List continued on next page.)

*Primary Examiner*—Diego Gutierrez
*Assistant Examiner*—Mirellys Jagan
(74) *Attorney, Agent, or Firm*—Finnegan, Henderson, Farabow, Garrett & Dunner, LLP

(57) ABSTRACT

A method of evaluating the level of anxiety and/or truthfulness of a person may include measuring the skin temperature of the person at at least three regions of the skin of the person, requesting the person to supply information, measuring the skin temperature at the at least three regions while the person supplies the information, and measuring the skin temperature at the at least three regions after the person supplies the information. The level of anxiety and/or truthfulness of the person may be determined based at least partially on a combination of the difference between the measured skin temperature of the person before the information is supplied and the measured skin temperature of the person while the information is supplied, and the difference between the measured skin temperature of the person while the information is supplied and the measured skin temperature of the person after the information is supplied.

17 Claims, 18 Drawing Sheets

OTHER PUBLICATIONS

Pavlidis, I., et al., "Seeing through the face of deception", *Nature*, vol. 415, Jan. 3, 2002, 1 page.

Pearson, H., "Thermal imaging May Detect Lying", *National Center for Policy Analysis*, Jan. 3, 2002, 2 pages.

"The Autonomic Nervous System", *Neuroscience for Kids*, date unknown, 5 pages.

"The Infrared", *The Electromagnetic Spectrum*, date unknown, 7 pages.

"Infrared cameras fill industrial inspection needs", *Sierra Pacific Infrared*, date unknown, 5 pages.

* cited by examiner

METHOD OF EVALUATING LEVEL OF ANXIETY OF PERSON BASED ON SKIN TEMPERATURE

This application claims the benefit under 35 U.S.C. § 119(e)(1) of provisional application No. 60/365,189, filed Mar. 19, 2002.

BACKGROUND OF THE INVENTION

1. Field of the Invention

The present invention relates to a method of evaluating the level of anxiety of a person. More particularly, the present invention relates to a method for evaluating the level of anxiety of a person when responding to a request for information. While the invention is subject to a wide range of applications, it may be especially suited for use as a method for increasing the security of locations against terrorist infiltration and/or attacks.

2. Description of the Related Art

In the latter part of the twentieth century and at the beginning of the new millennium, attempts to increase the security of businesses and government installations have become a higher priority. For example, attempts to accurately and quickly screen employees and interrogate criminals has become an important aspect of everyday life. Such attempts may be the result of a greater need to protect trade secrets, reduce liability due to employee criminal activity, reduce theft of property, and protect top secret information. In addition, the rise in identity theft has created a need for local government agencies, such as licensing agencies, to be able to verify a person's identity. Furthermore, a worldwide increase in terrorist activity has resulted in a greater need to quickly and accurately detect terrorists in order to prevent terrorist attacks. For example, following the terrorist attacks in the United States on Sep. 11, 2001, a greater emphasis has been placed on screening airline passengers to prevent a recurrence of future similar terrorist attacks.

Some conventional methods for increasing the security of various businesses and government installations include the use of the traditional polygraph test sometimes referred to as a "lie detector test," X-ray machines, metal detectors, and bomb detectors. These methods, however, have proven less reliable than needed due to various shortcomings. For example, the traditional polygraph test typically relies on the measurement of, for example, a person's breathing, blood flow, and perspiration rates. Some of the inherent shortcomings of a polygraph test include the need for a highly trained technician to administer the test, the need for a complex monitoring apparatus that includes electric leads that must be attached to the person being tested, the need for the test subject's cooperation, and the need for an elaborate and time consuming testing procedure requiring numerous questions. In addition, research has shown that some people can reduce the accuracy of a polygraph test through training or other means. Such shortcomings render the polygraph test generally unsuitable for many applications such as airport screenings.

Like the polygraph test, X-ray machines, metal detectors, and bomb detectors have been shown to be somewhat unreliable as evidenced by the terrorist attacks of Sep. 11, 2001. For example, X-ray machines may be defeated by cleverly disguising weapons, metal detectors may be fooled by the use non-metallic weaponry, and bomb detectors may likewise be defeated by clever concealment of explosive devices. Furthermore, the terrorist attacks of Sep. 11, 2001, illustrated that the airplanes themselves may be converted into particularly effective weapons capable of inflicting thousands of deaths.

In light of the above-mentioned shortcomings of conventional methods of increasing security, there is a need for methods of increasing security that are more reliable and more efficient. For example, there is need for a method of increasing security that, among other things, does not require highly trained technicians for effectiveness, that is non-invasive, that does not create lengthy delays when used to screen large numbers of people, that does not require the cooperation of the person being screened, and that has an increased reliability.

SUMMARY OF THE INVENTION

Accordingly, the present invention is directed to a method of evaluating the level of anxiety of a person that substantially obviates one or more of the problems associated with limitations and disadvantages of the above-mentioned conventional methods.

In the following description, certain aspects and embodiments will become evident. It should be understood that the invention, in its broadest sense, could be practiced without having one or more features of these aspects and embodiments. It should be understood that these aspects and embodiments are merely exemplary.

In one aspect, as embodied and broadly described herein, the invention includes a method of measuring changes in skin temperature of a person. The method may include providing a device for measuring skin temperature, measuring the skin temperature of the person at at least three regions of the skin of the person, requesting the person to supply information, and measuring the skin temperature at the at least three regions while the person supplies the information. The method may further include measuring the skin temperature at the at least three regions after the person supplies the information, and determining the difference between the measured skin temperature of the person before the information is supplied and the measured skin temperature of the person while the information is supplied, and the difference between the measured skin temperature of the person while the information is supplied and the measured skin temperature of the person after the information is supplied.

The term "providing" is used in a broad sense, and refers to, but is not limited to, making available for use, enabling usage, giving, supplying, obtaining, getting a hold of, acquiring, purchasing, selling, distributing, possessing, making ready for use, and/or placing in a position ready for use.

In another aspect, the device for measuring skin temperature may include a thermal imaging device.

In an additional aspect, one of the at least three regions may include the neck of the person. In yet another aspect, one of the at least three regions may include the forehead of a person. In still another aspect, one of the at least three regions may include substantially the entire face and neck of the person.

According to an additional aspect, determining the difference in skin temperature may include determining the amount of increase in skin temperature for each of the at least three regions from the skin temperature measured before the information is supplied to the skin temperature measured while the information is supplied, and determining the amount of decrease in skin temperature for each of the at least three regions from while the information is supplied to after the information is supplied. For example, if any three of the amounts of increase and decrease in skin temperature are determined to be at least a predetermined amount of change, the person is determined to be anxious. For example, if any three of the amounts of increase and decrease in skin temperature are determined to be at least a predetermined amount of change, the person is determined to be untruthful. For example, if the predetermined amount of change is one half of one degree Fahrenheit, the person is determined to be providing an untruthful response.

In a further aspect, requesting the person to supply information may include asking the person at least one question.

In yet another aspect, the method may include providing a device for automatically determining the truthfulness of the person and using the device to automatically determine the truthfulness of the person based on skin temperature data supplied to the device.

In still another aspect, the measuring of the skin temperature of the person is unknown to the person whose skin temperature is being measured.

In a further aspect, a method of evaluating the truthfulness of a person based on information supplied by the person may include providing a device for measuring skin temperature, measuring the skin temperature of the person at at least three regions of the skin of the person, requesting the person to supply information, measuring the skin temperature at the at least three regions while the person supplies the information, and measuring the skin temperature at the at least three regions after the person supplies the information. The method may further include determining the truthfulness of the person based at least partially on a combination of the difference between the measured skin temperature of the person before the information is supplied and the measured skin temperature of the person while the information is supplied, and the difference between the measured skin temperature of the person while the information supplied and the measured skin temperature of the person after the information is supplied.

According to yet another aspect, a method of increasing security of at least one of an organization, a location, and a transportation device may include providing a device for measuring skin temperature, measuring the skin temperature of the person at at least three regions of the skin of the person, requesting the person to supply information, measuring the skin temperature at the at least three regions while the person supplies the information, and measuring the skin temperature at the at least three regions after the person supplies the information. The method may further include determining the truthfulness of the person based at least partially on a combination of the difference between the measured skin temperature of the person before the information is supplied and the measured skin temperature of the person while the information is supplied, and the difference between the measured skin temperature of the person while the information is supplied and the measured skin temperature of the person after the information is supplied.

In another aspect, a method of evaluating the truthfulness of a person based on information supplied by the person may include providing a device for measuring skin temperature, measuring the skin temperature of the neck of the person, requesting the person to supply information, measuring the skin temperature of the neck of the person while the person supplies the information, and measuring the skin temperature of the neck of the person after the person supplies the information. The method may further include determining the truthfulness of the person based at least partially on a combination of the difference between the measured skin temperature of the neck of the person before the information is supplied and the measured skin temperature of the neck of the person while the information is supplied, and the difference between the measured skin temperature of the neck of the person while the information is supplied and the measured skin temperature of the neck of the person after the information is supplied.

Aside from the procedural arrangements set forth above, the invention could include a number of other arrangements, such as those explained hereinafter. It is to be understood, that both the foregoing description and the following description are exemplary.

The accompanying drawings are incorporated in and constitute a part of this specification. The drawings illustrate exemplary embodiments of the invention and, together with the description, serve to explain some principles of the invention.

DESCRIPTION OF EMBODIMENTS

Figure 1:
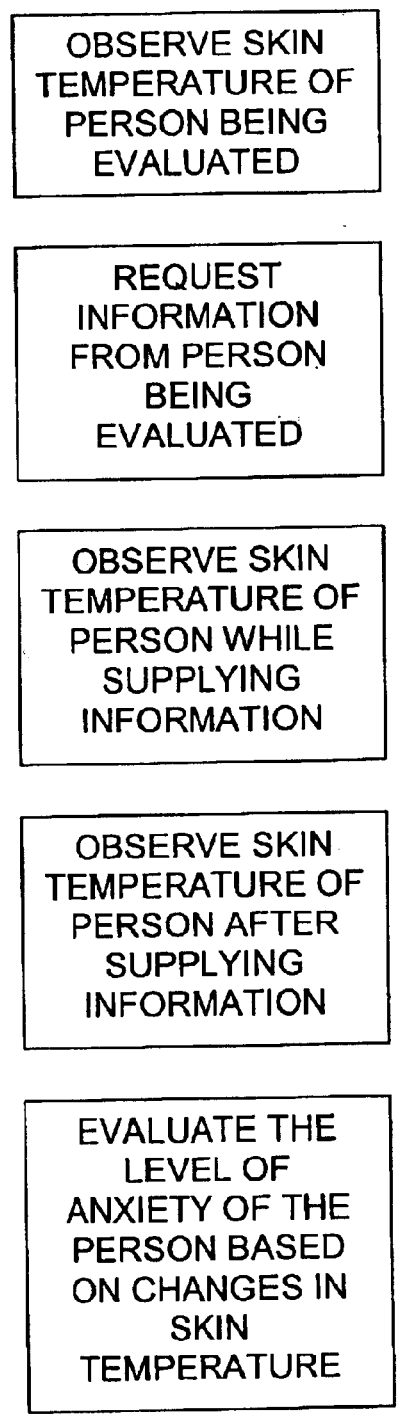
FIG. 1 is a block diagram of an exemplary embodiment of a method according to one aspect of the invention.

Reference will now be made in detail to some possible embodiments of the invention, examples of which are illustrated in the accompanying drawings. Wherever possible, the same reference numbers are used in the drawings and the description to refer to the same or like parts.

The exemplary embodiment of a method of evaluating the level of anxiety of a person is depicted in the block diagram of FIG. 1.

As embodied herein and referring to FIG. 1, a method of evaluating the level of anxiety of a person includes providing a device for measuring skin temperature, measuring the skin temperature of the person at at least three regions of the skin of the person, requesting the person to supply information, measuring the skin temperature at the at least three regions while the person supplies the information, measuring the skin temperature at the at least three regions after the person supplies the information, and determining the level of anxiety of the person based at least partially on a combination of the difference between the measured skin temperature of the person before the information is supplied and the measured skin temperature of the person while the information is supplied, and the difference between the measured skin temperature of the person while the information is supplied and the measured skin temperature of the person after the information is supplied.

The method according to some embodiments may be related to the fact that changes in skin temperature of a person may result from an involuntary reaction that is controlled by the autonomic nervous system (ANS). The ANS controls many of the functions of the internal organs, such as the organs of the digestive system and heart over which humans do not have voluntary control.

The sympathetic nervous system (SNS) and parasympathetic nervous system (PNS) are portions of the ANS that may be respectively activated before and after a person is exposed to an anxious situation, for example, a startling situation. The SNS may be activated in response to situations which tend to induce a "fight or flight" response. When humans are exposed to an alarming and/or threatening situation, the SNS quickly and involuntarily activates a response in humans to prepare to, for example, ward off an attacker and/or flee the area associated with the perceived danger. The SNS response may often result in an increased heart rate, a corresponding increased flow of blood to the limbs, and a dilation of the blood vessels in the face, ears, and neck, that results in an increase in the temperature and heat emitted from these areas.

In contrast, the PNS counteracts the SNS when the perceived anxious situation abates, and decreases the heart rate and blood flow. As a result, the heat and temperature in, for example, the face, ears, and neck decreases. In other words, when a person encounters a situation that renders them anxious, the SNS involuntarily creates a reaction that increases the temperature of portions of the person's skin. When the situation that has caused the anxiousness is no longer perceived, however, the PNS involuntarily decreases the temperature of portions of the person's skin that had previously been increased.

The method according to some embodiments of the invention takes advantage of the interaction of between the SNS and the PNS. For example, the level of anxiousness of a person may be determined by monitoring changes in temperature of portions of the person's skin. If the person displays an increase and corresponding decrease in skin temperature as a result of the exposure to and withdrawal of a particular anxiety causing stimulus or event, the person has displayed a heightened level of anxiety during the exposure.

In addition to responses associated with exposure to anxiety causing events, a heightened level of anxiety may also be associated with untruthfulness and/or deception. Hence, by virtue of the link between changes in skin temperature and anxiety, the method according to some embodiments of the invention may be used to detect untruthfulness and/or deception by the person exhibiting corresponding changes in skin temperature when responding to, for example, requests for information. In short, the method may be used to detect when a person is providing untruthful and/or deceptive responses to requests to supply information. Furthermore, changes in skin temperature may be monitored via, for example, thermal imaging devices that do not require physical attachment to a person being monitored for skin temperature changes and that may be placed in a relatively remote location a relatively large distance from the person being monitored.

Advantages of such a method may be numerous. For example, by virtue of the fact that changes in skin temperature resulting from activation of the SNS and PNS are involuntary, it may be quite difficult for a person to prevent themselves from exhibiting changes in skin temperature when responding to requests for information in an untruthful and/or deceptive manner. Furthermore, because a person's skin temperature may be monitored remotely, for example, without the person's knowledge and/or cooperation, the person being requested to provide information may not even be aware that they should attempt to avoid exhibiting changes in skin temperature. In addition, because skin temperature changes occur rapidly and involuntarily, it may not be necessary to rely on highly skilled investigators in order to analyze the significance of the temperature changes.

Figure 2:
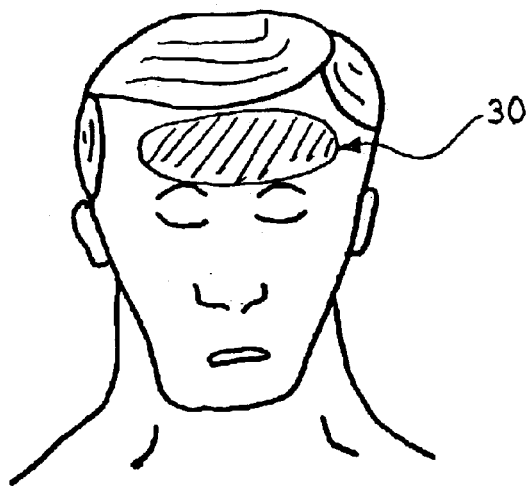
FIG. 2 is schematic diagram of a forehead region of the skin of a person.
Figure 3:
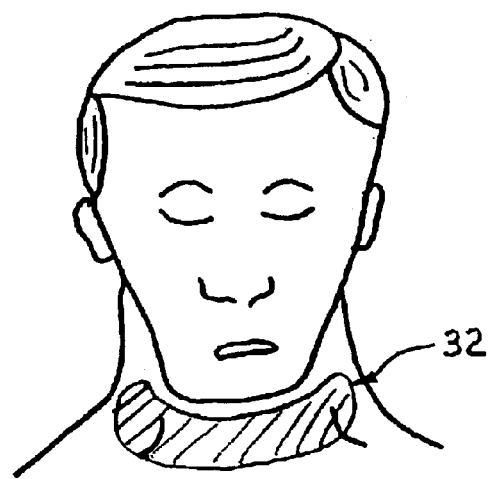
FIG. 3 is schematic diagram of a neck region of the skin of a person.
Figure 4:
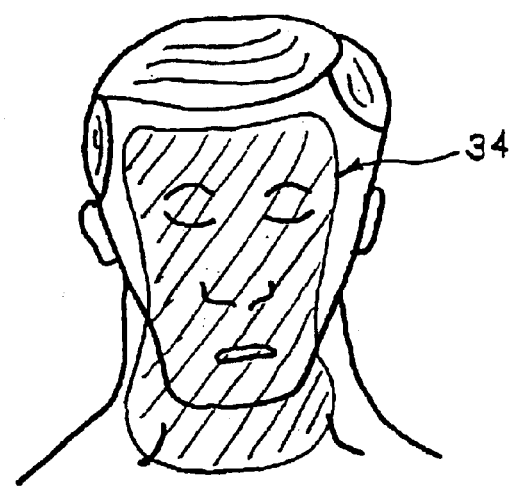
FIG. 4 is schematic diagram of an overall face region of the skin of a person.
Figure 5:
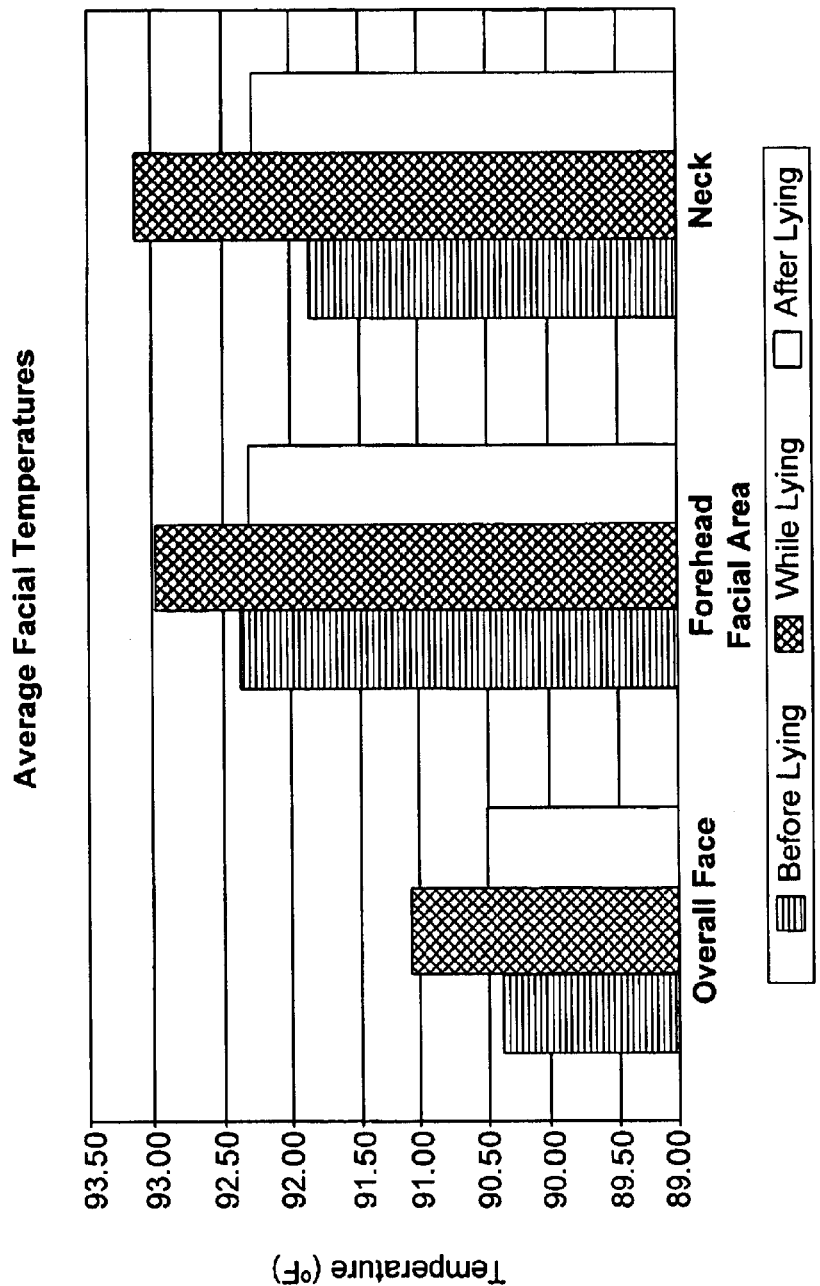
FIG. 5 is a bar graph of combined test results for a population of subjects subjected to a method according to one aspect of the invention.
Figure 6:
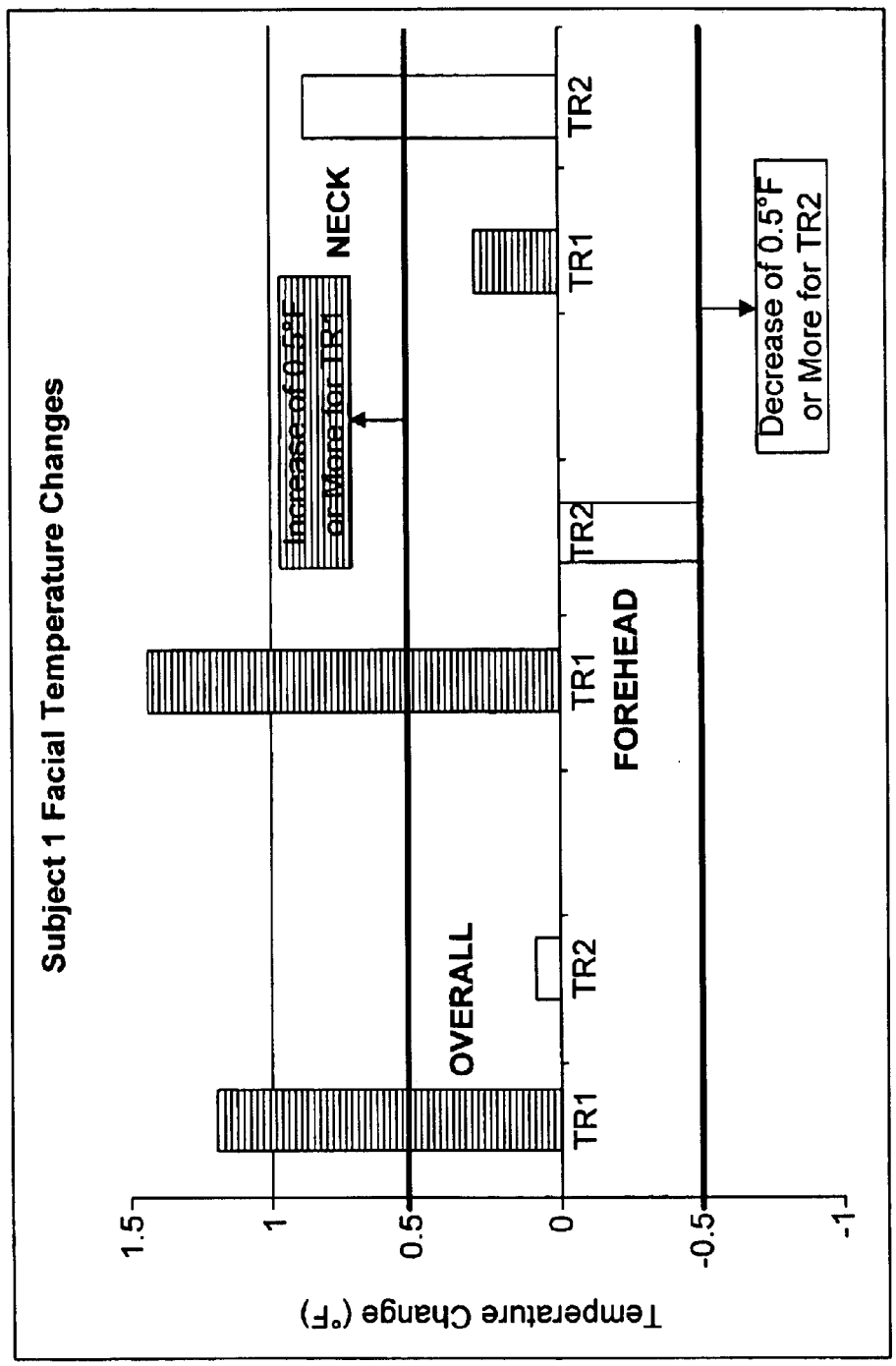
FIG. 6 is a bar graph of test results for a subject subjected to a method according to one aspect of the invention.

It has been found that different regions of a person's skin exhibit different temperature changes in response to activation of the SNS and PNS. For example, the regions associated with a person's forehead region 30, as shown in FIG. 2, neck region 32, as shown in FIG. 3, and overall face and neck region 34, as shown in FIG. 4, exhibit relatively pronounced changes in skin temperature as a result of a person's exposure to situations that create anxiety.

For example, in tests conducted using fifteen subjects whose skin temperature changes were observed before, during, and after responding to requests for information, rapid increases and decreases in skin temperature were observed as shown in Table 1, below. After reviewing the test data, it was determined that the forehead region 30, the neck region 32, and the overall face and neck region 34 displayed an enhanced increase and decrease in skin temperature when the subject responded untruthfully to requests for information.

TABLE 1

Facial Temperature (° F.)

| | Overall Face | | | Forehead | | | Neck | | |
|---|---|---|---|---|---|---|---|---|---|
| | Before Lying | While Lying | After Lying | Before Lying | While Lying | After Lying | Before Lying | While Lying | After Lying |
| Subject 1 | 91.80 | 93.00 | 93.10 | 92.90 | 94.30 | 93.80 | 92.60 | 92.90 | 93.80 |
| Subject 2 | 92.60 | 93.40 | 93.10 | 93.00 | 93.80 | 93.40 | 93.30 | 94.00 | 93.80 |
| Subject 3 | 91.40 | 92.20 | 91.30 | 92.90 | 94.00 | 93.30 | 93.90 | 95.20 | 93.90 |
| Subject 4 | 87.50 | 88.90 | 88.10 | 92.00 | 93.00 | 92.50 | 90.30 | 91.40 | 90.30 |
| Subject 5 | 90.50 | 91.00 | 90.20 | 91.30 | 91.90 | 90.90 | 91.40 | 92.70 | 91.40 |
| Subject 6 | 91.00 | 91.80 | 91.40 | 93.10 | 94.00 | 93.40 | 92.90 | 93.90 | 93.30 |
| Subject 7 | 92.0 | 92.20 | 90.80 | 93.20 | 91.90 | 89.90 | 91.80 | 96.80 | 92.20 |
| Subject 8 | 91.00 | 91.30 | 91.00 | 90.50 | 91.40 | 90.60 | 91.90 | 92.10 | 92.20 |
| Subject 9 | 90.60 | 91.20 | 91.10 | 93.40 | 93.80 | 93.40 | 90.30 | 92.60 | 91.90 |
| Subject 10 | 92.40 | 92.70 | 90.90 | 92.00 | 92.20 | 90.50 | 93.40 | 94.60 | 92.00 |
| Subject 11 | 88.30 | 89.00 | 88.20 | 91.90 | 92.70 | 92.20 | 91.00 | 91.70 | 91.20 |
| Subject 12 | 88.30 | 89.90 | 89.10 | 91.90 | 93.30 | 92.30 | 92.60 | 93.70 | 92.90 |
| Subject 13 | 91.80 | 92.00 | 91.50 | 92.90 | 93.20 | 92.70 | 91.80 | 92.00 | 91.50 |
| Subject 14 | 85.00 | 88.40 | 88.80 | 91.30 | 92.30 | 92.00 | 87.10 | 89.70 | 91.10 |
| Subject 15 | 91.20 | 90.90 | 90.60 | 92.70 | 92.80 | 92.70 | 92.30 | 92.50 | 91.40 |
| Average | 90.36 | 91.06 | 90.48 | 92.33 | 92.97 | 92.24 | 91.77 | 93.50 | 92.19 |

The testing procedure used to acquire the data listed in Table 1 will now be described in some detail. In a small conference room, fifteen subjects, all volunteers, were seated at a small table across from a person who interviewed the subjects. Each subject was interviewed individually without the presence of the other subjects in the room. In order to monitor changes in the subject's skin temperature, a thermal imaging device was positioned generally four feet away from each of the subjects during the interview. The thermal imaging device used in the testing procedure was a FLIR Thermacam PM 595 (Thermacam) that incorporates a microbolometer detector. The Thermacam is non-cooled and operates in the spectral range from about seven and one-half microns to about thirteen microns, and has a sensitivity of about eight hundredths of a degree Celsius at about thirty degrees Celsius. Although the Thermacam was used in this test, it is exemplary only, and it is contemplated that other temperature and/or heat detecting devices and/or methods could be used when employing embodiments of the method of the invention.

During the testing, the testing procedure was explained and each subject was told that they would be providing both truthful and untruthful responses to requests for information. During the testing, the person requesting the information, the requester, was able to monitor the images generated by the thermal imaging device on a television monitor. In addition, the requester was able to store discrete images for later analysis by selectively triggering the thermal imaging device.

The requester began each interview with requests for information that would tend to relax each subject by requesting truthful information relating to the subject's name, birthplace, whether they had attended college, if they had attended college, where, and how long they had worked for their employer. Following this initial portion of the interview, each subject was asked to provide information responsive to three separate requests such that their responses would include two truthful responses and one untruthful response. The subjects were also instructed to draw a number from a hat that would correspond to the number of the request from among the three to which they were to respond untruthfully. Unbeknownst to the subjects, however, all the numbers in the hat were "1", thus instructing them to provide an untruthful response to the first of the three requests. In this manner, the requester always knew which responses were untruthful in order to standardize the testing procedure.

The requester's first request for information included asking the subjects to describe their first real job, the people for whom they worked, how they commuted, and what their duties were. During each subject's response, the requester triggered the thermal imaging device so that discrete images were stored for later analysis. Following the initial, untruthful responses, the subjects were requested to provide truthful information relating to the house where they grew up and leisure activities that they enjoy. As before, the thermal imaging device was triggered to store discrete images while each subject responded truthfully to those requests for information.

Following the testing procedure, the stored images from the thermal imaging device were analyzed in order to determine any patterns and/or trends that might be useful in evaluating, for example, the truthfulness of responses to requests for information. Representative data is provided in Table 1 and in FIGS. 5-20. After careful review of the thermal stored images, it was determined that the forehead region 30, the neck region 32, and the overall face and neck region 34 of the subjects exhibited more pronounced skin temperature fluctuations than other regions of the skin observed, which correlated to the truthfulness of the responses provided by the subjects.

In addition, from among those three regions, two temperature change transitions were generally exhibited by those regions that correlated to the truthfulness of the responses. The first transition (TR1 as shown in FIGS. 6-20) occurred between the time before the subjects were asked to provide untruthful responses and the time during which the subjects were providing untruthful responses. The second transition (TR2 as shown in FIGS. 6-20) occurred between the time during which the subjects were providing untruthful responses and the time after the subjects provided untruthful responses. During the first transition TR1, the forehead region 30, the neck region 32, and the overall face and neck region 34 tended to exhibit an observable increase in temperature. During the second transition TR2, the forehead region 30, the neck region 32, and the overall face and neck region 34 tended to exhibit an observable decrease in temperature.

Figure 7:
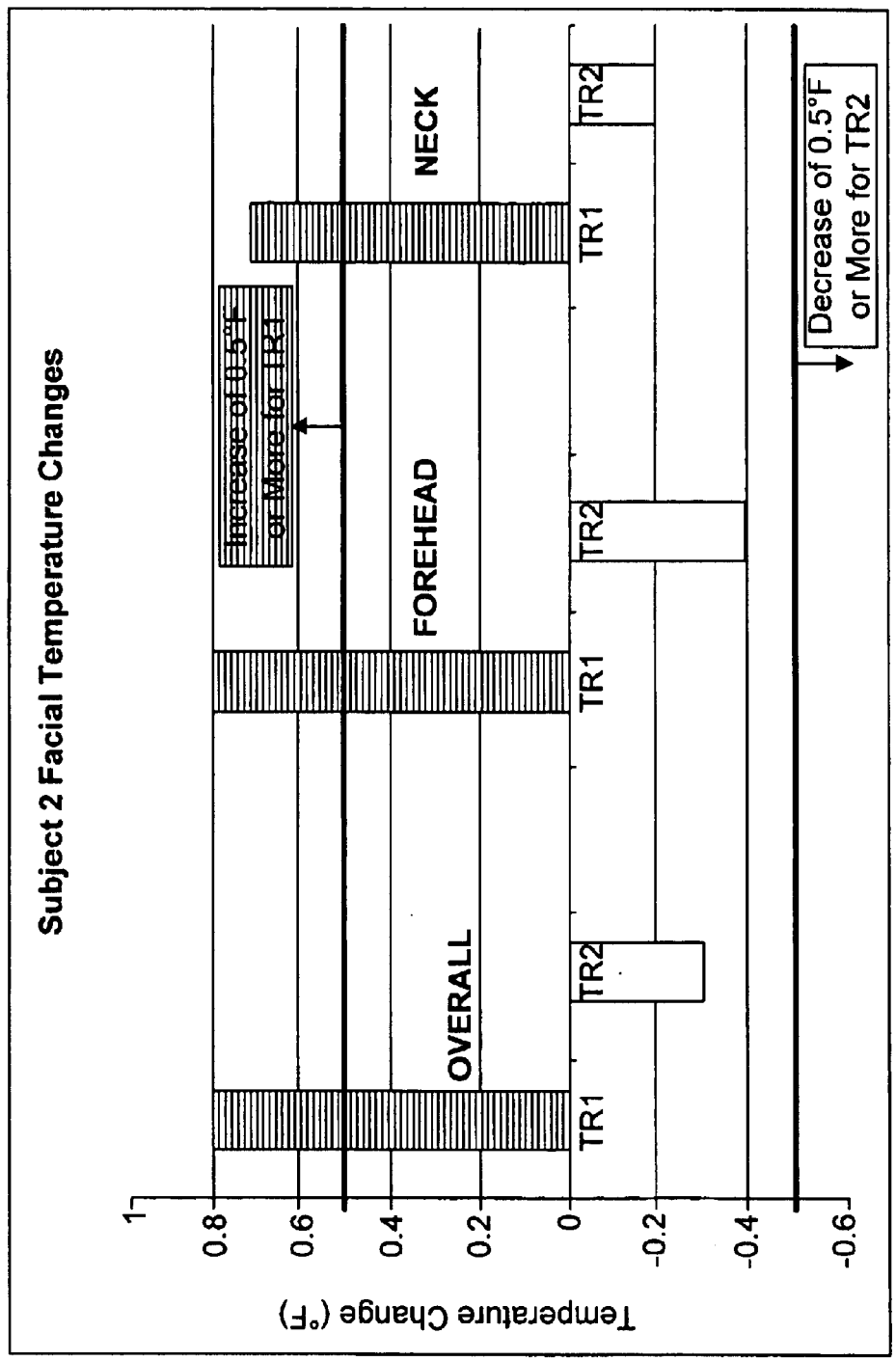
FIG. 7 is a bar graph of test results for another subject subjected to a method according to one aspect of the invention.
Figure 8:
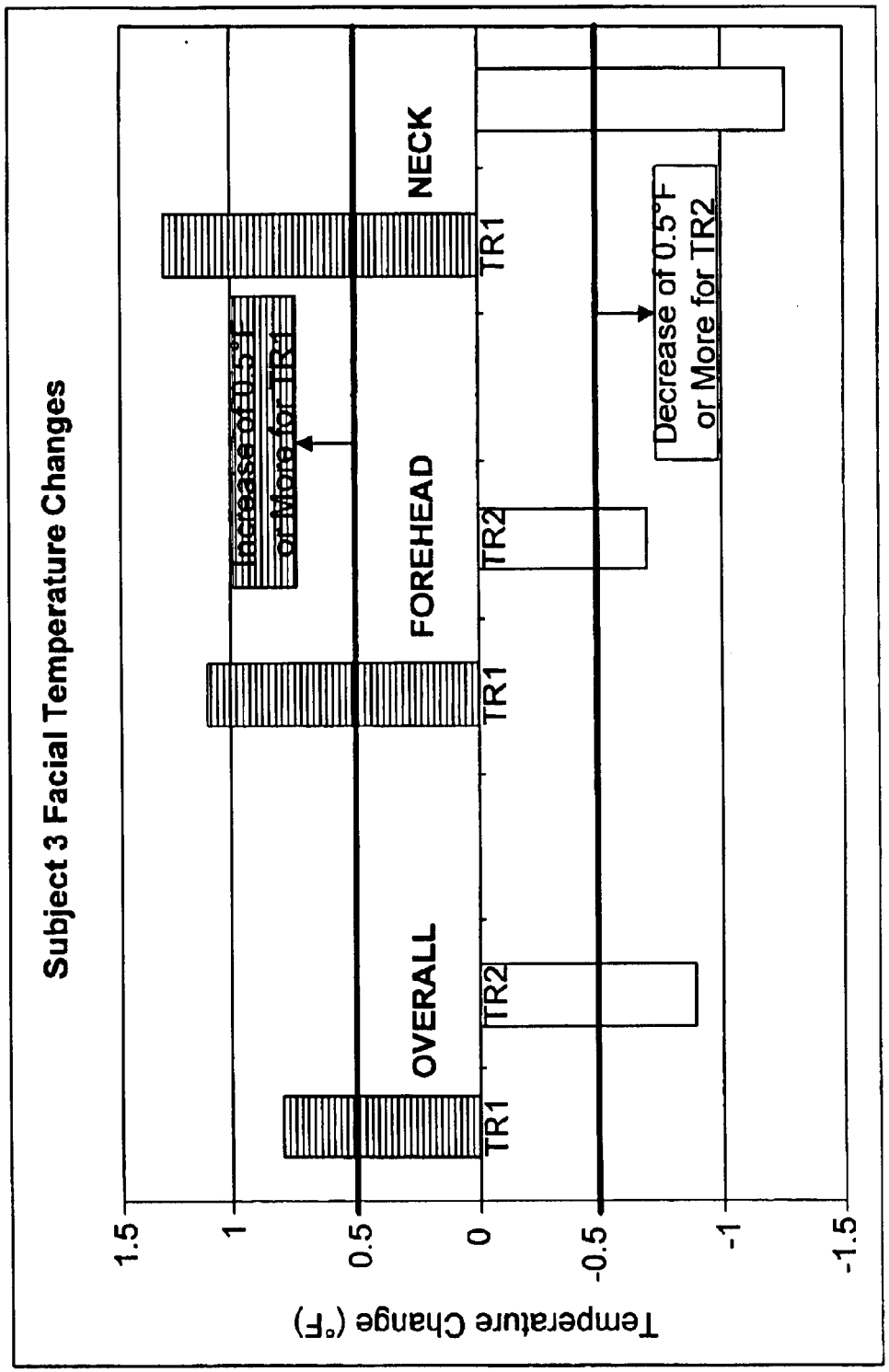
FIG. 8 is a bar graph of test results for another subject subjected to a method according to one aspect of the invention.
Figure 9:
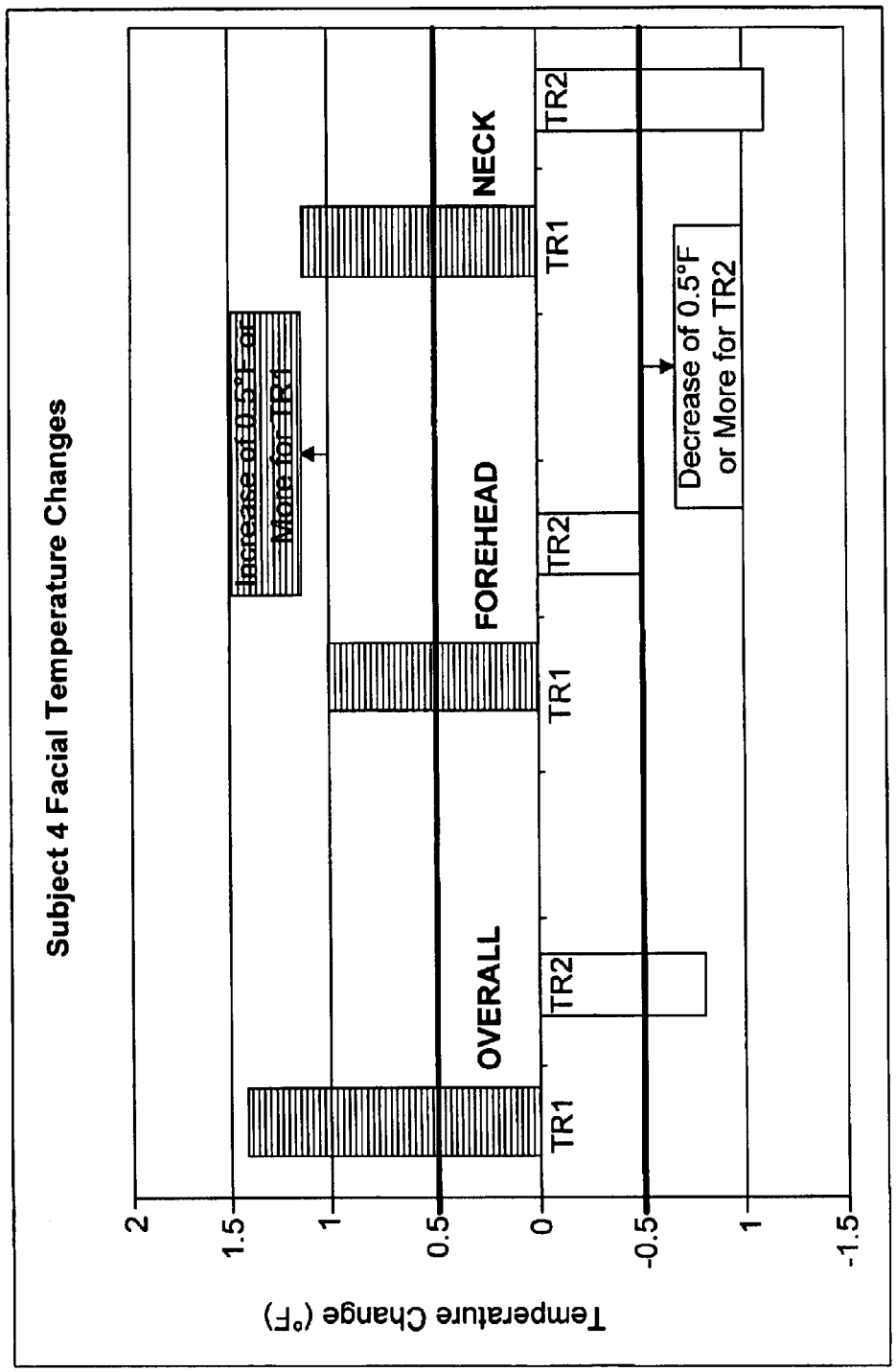
FIG. 9 is a bar graph of test results for another subject subjected to a method according to one aspect of the invention.
Figure 10:
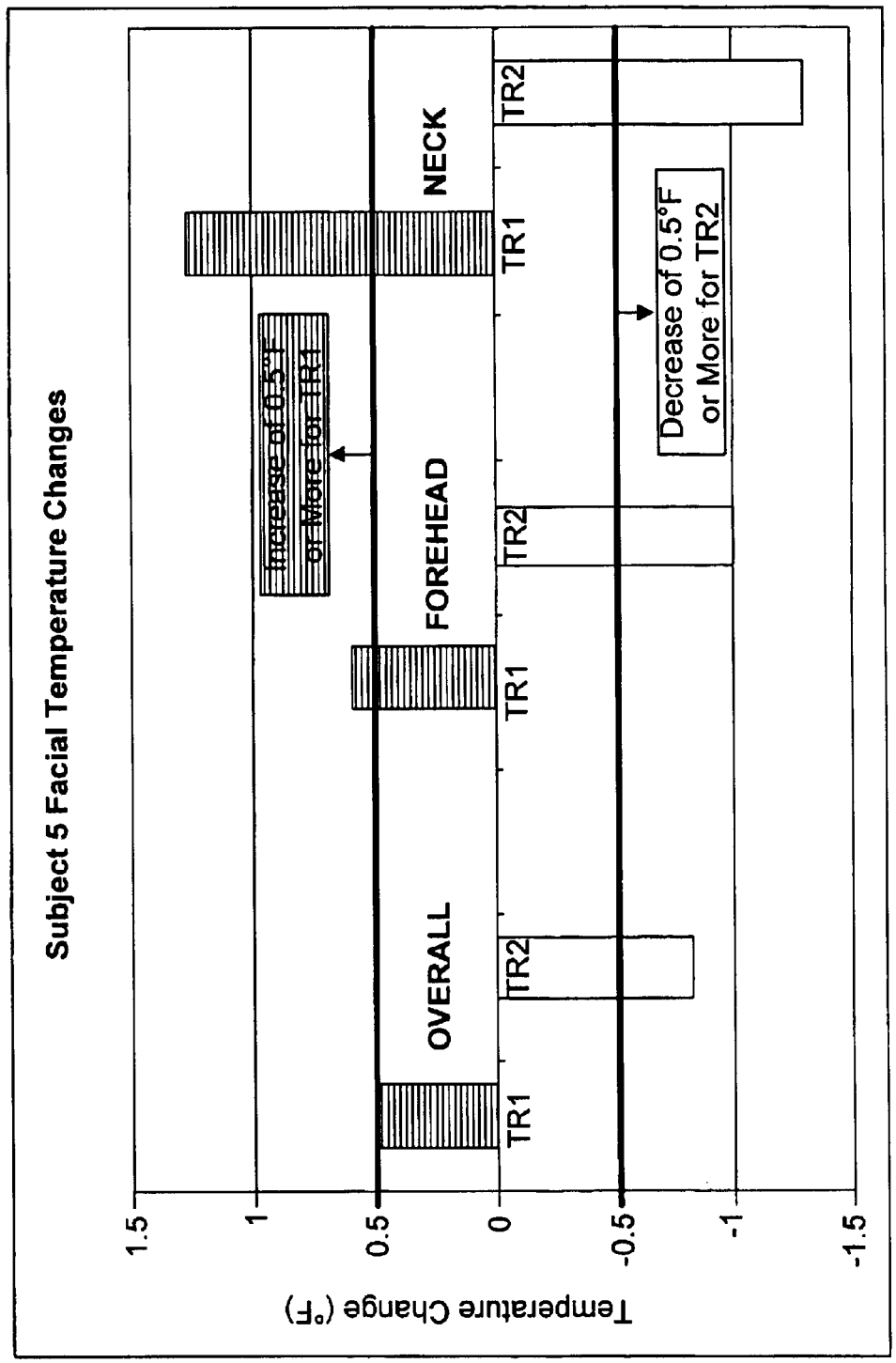
FIG. 10 is a bar graph of test results for another subject subjected to a method according to one aspect of the invention.
Figure 11:
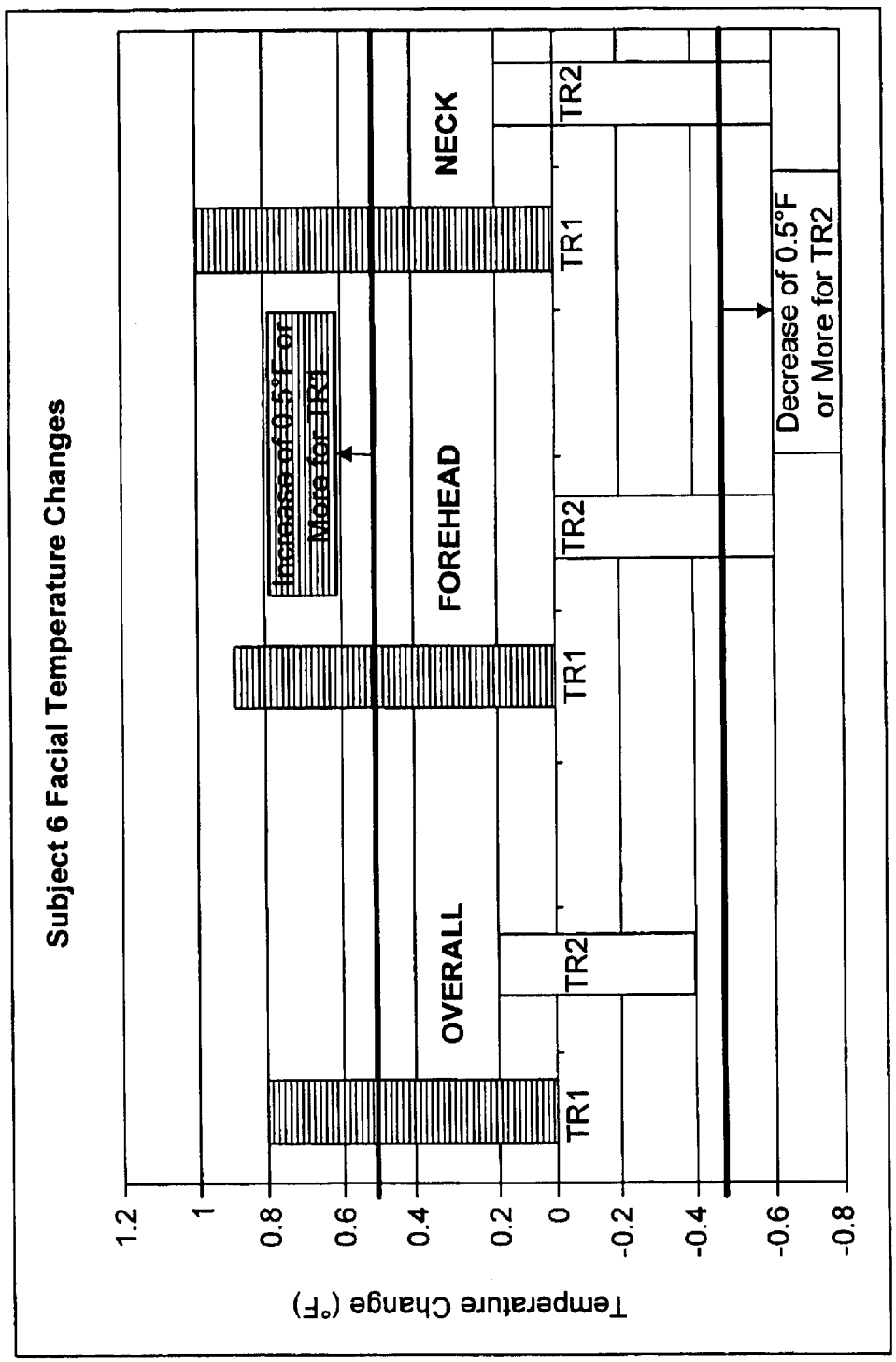
FIG. 11 is a bar graph of test results for another subject subjected to a method according to one aspect of the invention.
Figure 12:
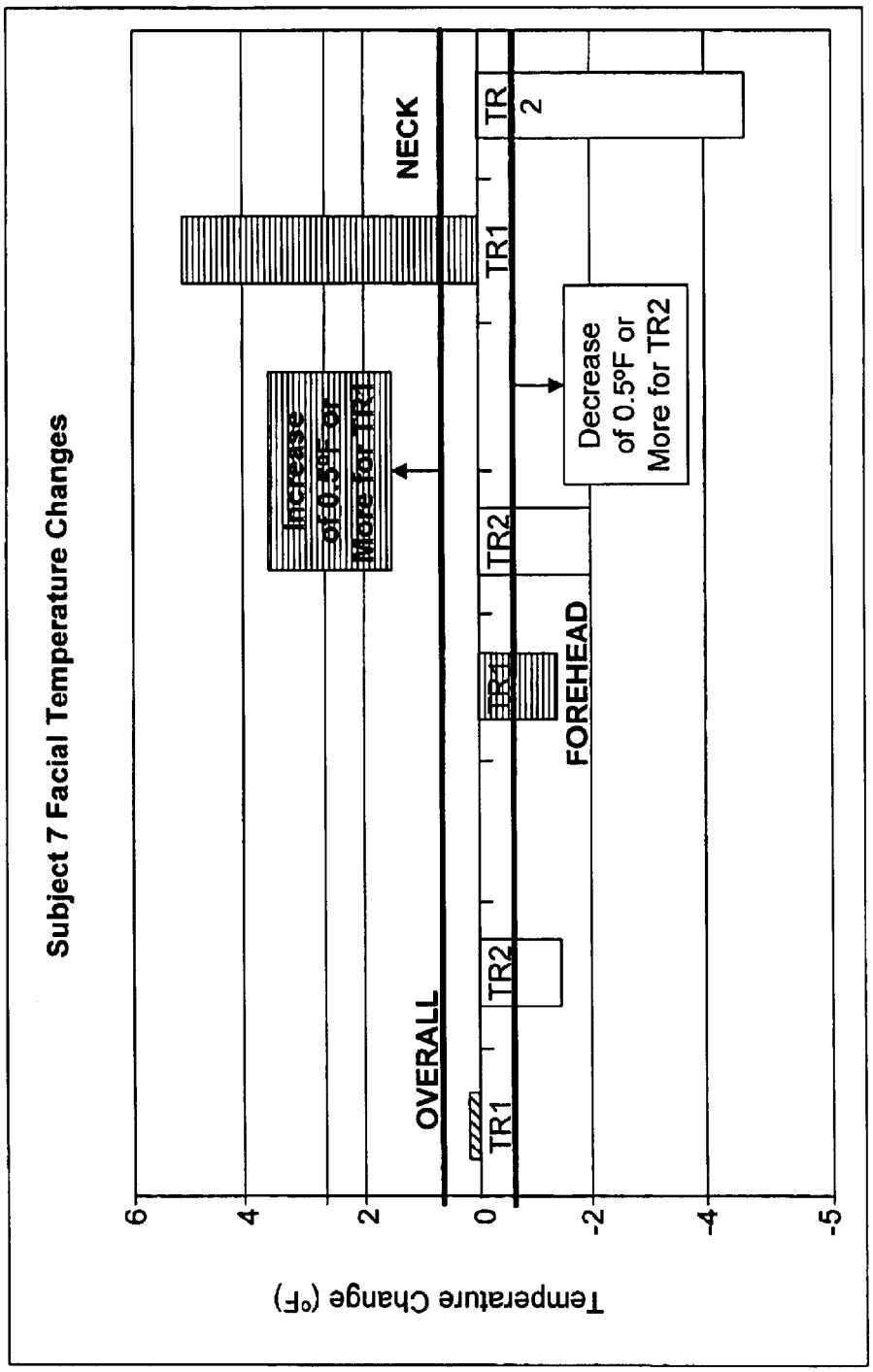
FIG. 12 is a bar graph of test results for another subject subjected to a method according to one aspect of the invention.
Figure 13:
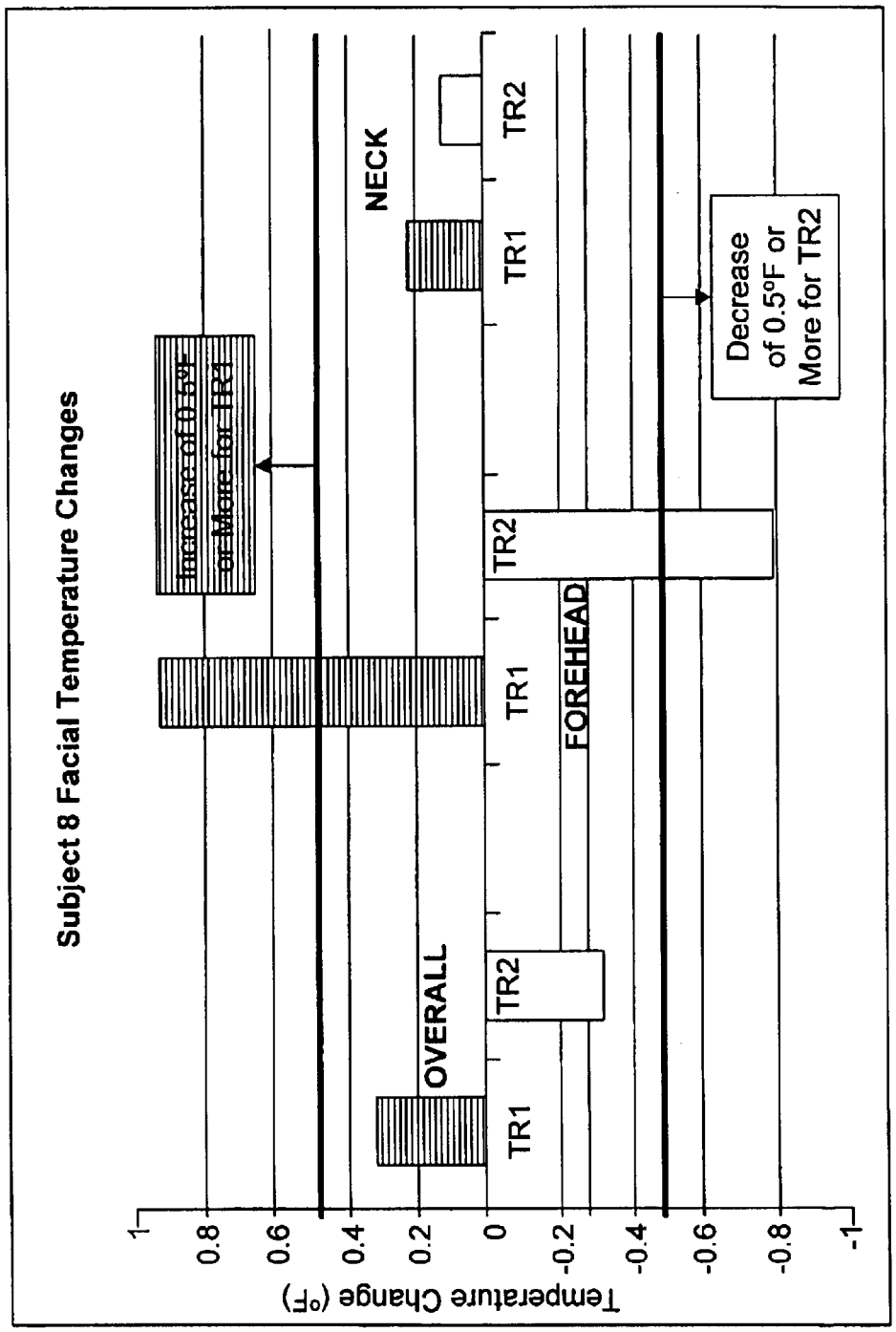
FIG. 13 is a bar graph of test results for another subject subjected to a method according to one aspect of the invention.
Figure 14:
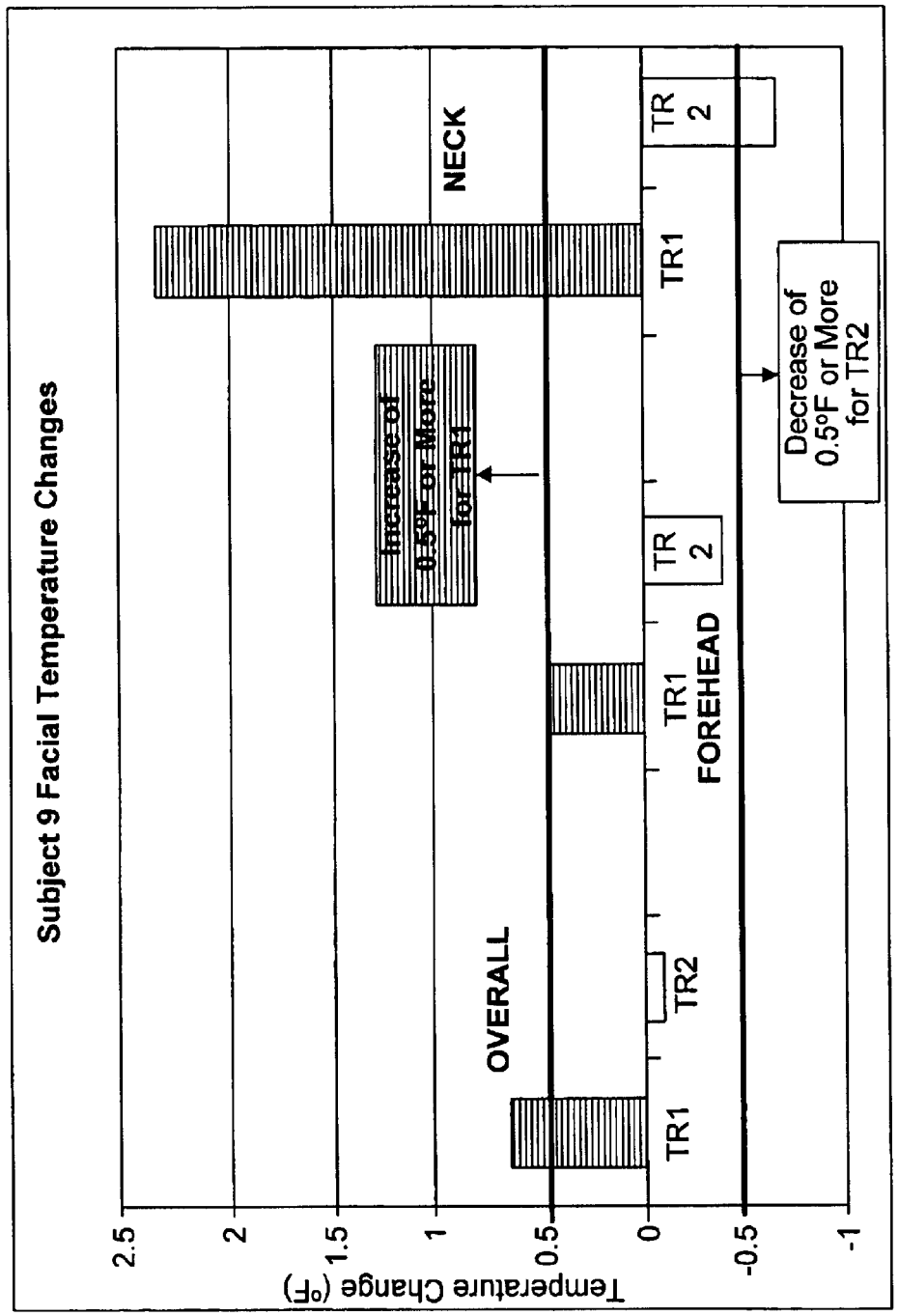
FIG. 14 is a bar graph of test results for another subject subjected to a method according to one aspect of the invention.
Figure 15:
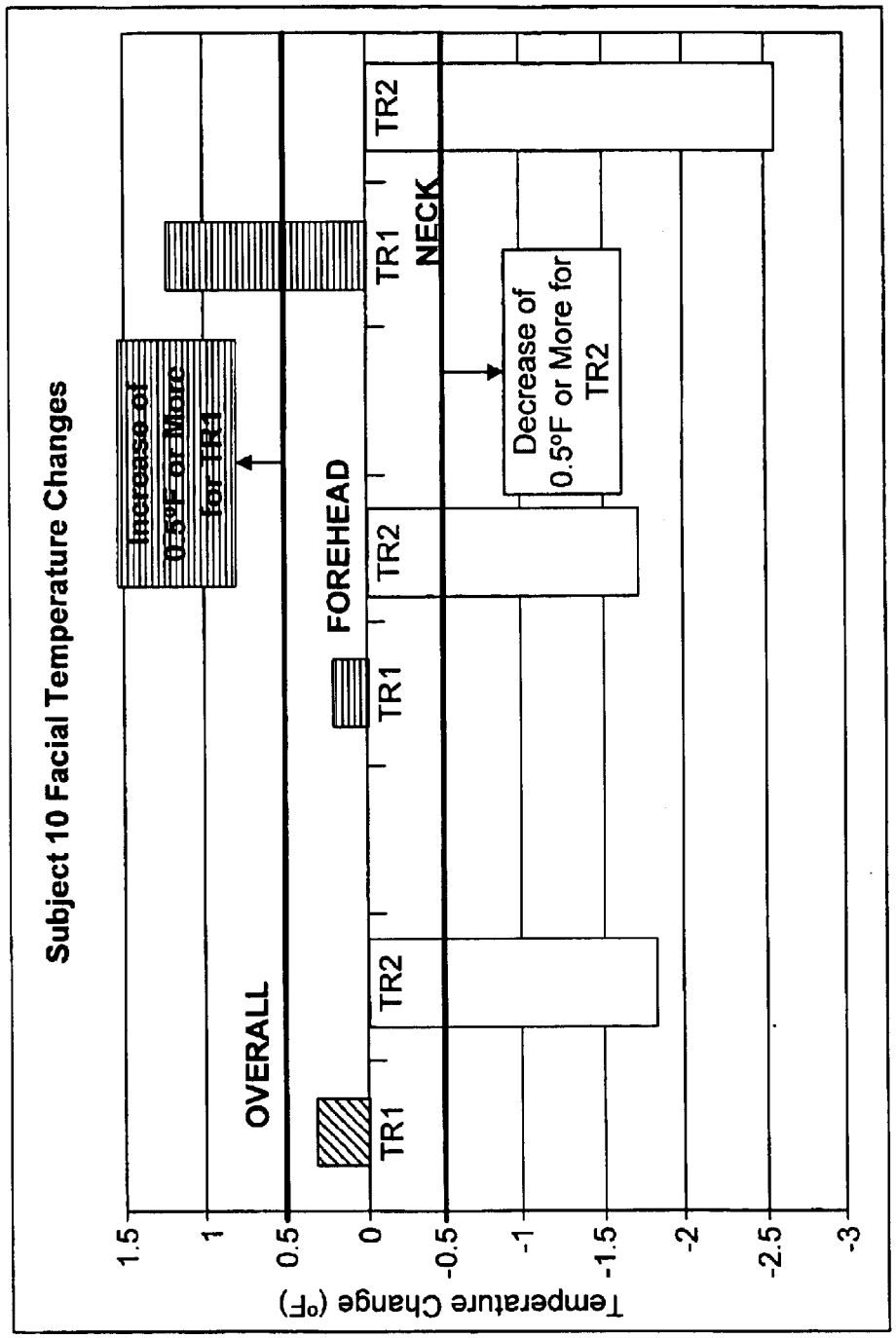
FIG. 15 is a bar graph of test results for another subject subjected to a method according to one aspect of the invention.
Figure 16:
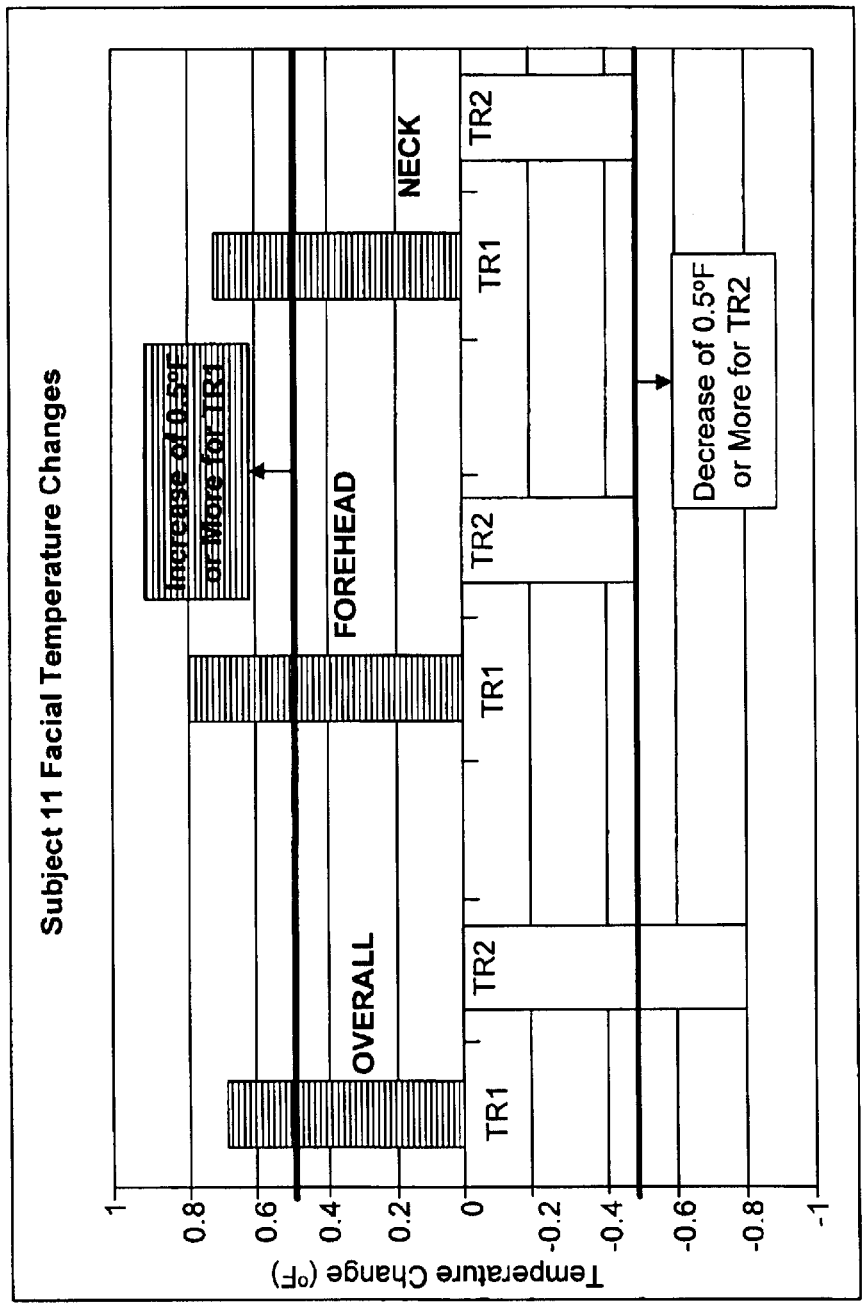
FIG. 16 is a bar graph of test results for another subject subjected to a method according to one aspect of the invention.
Figure 17:
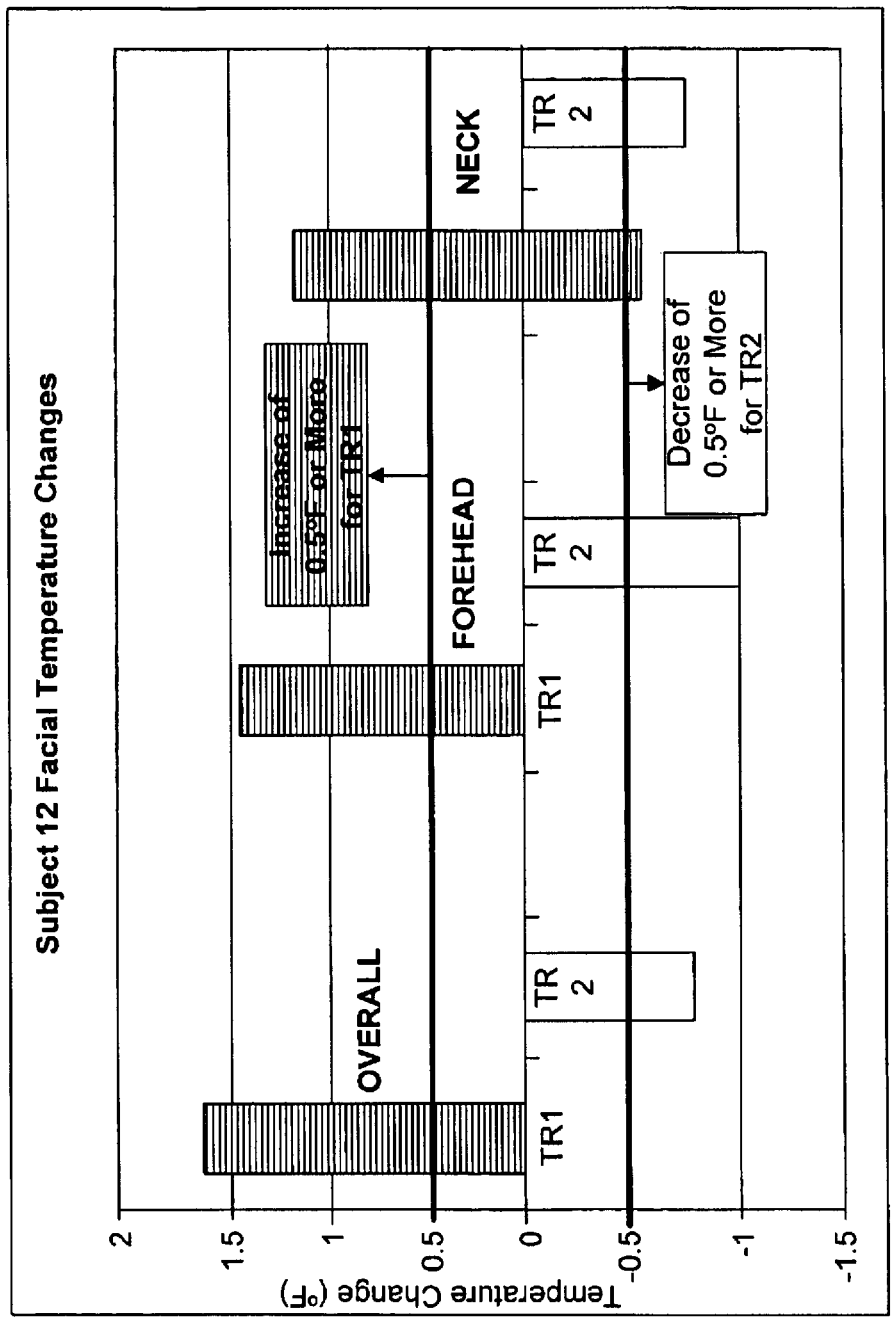
FIG. 17 is a bar graph of test results for another subject subjected to a method according to one aspect of the invention.
Figure 18:
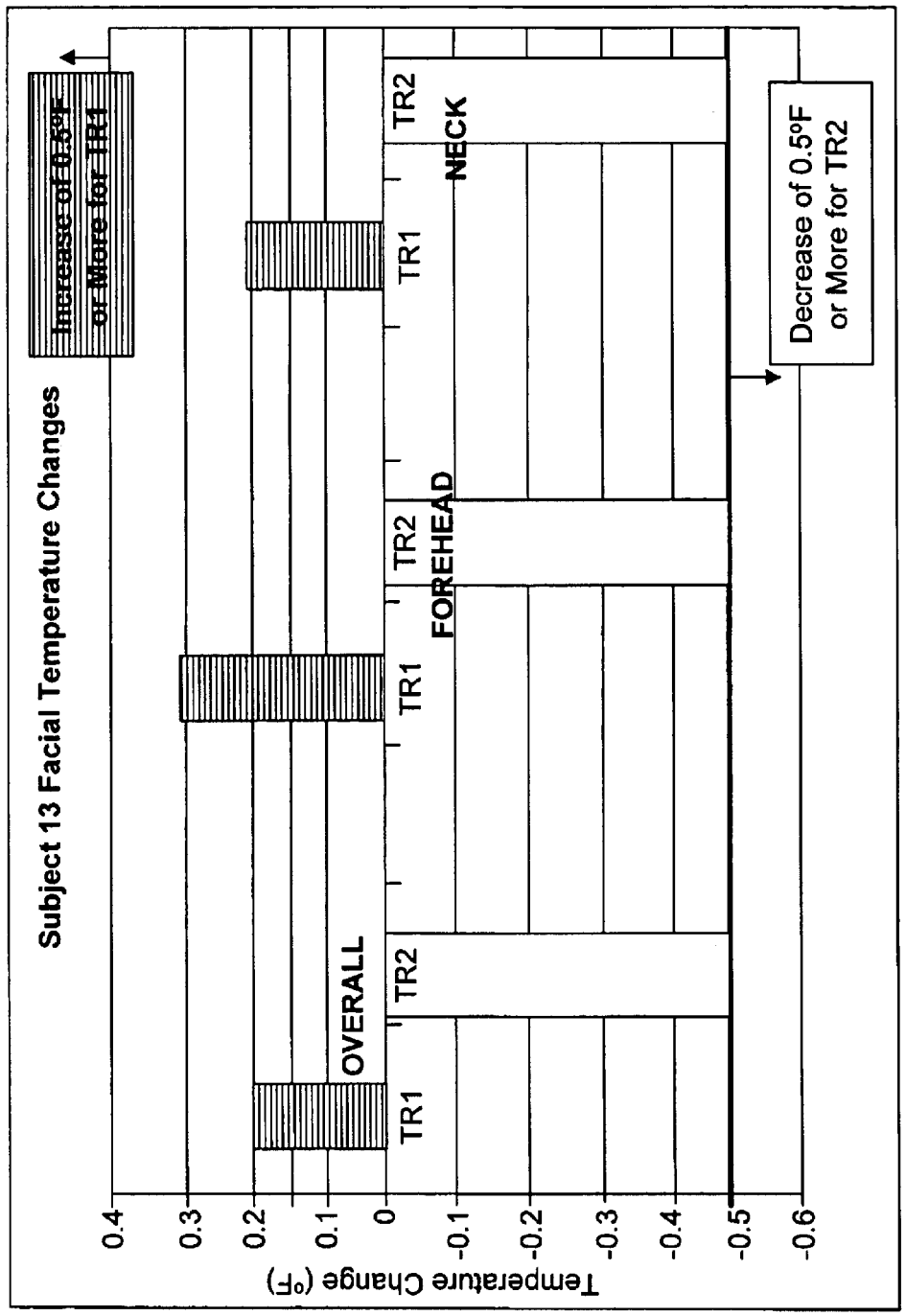
FIG. 18 is a bar graph of test results for another subject subjected to a method according to one aspect of the invention.
Figure 19:
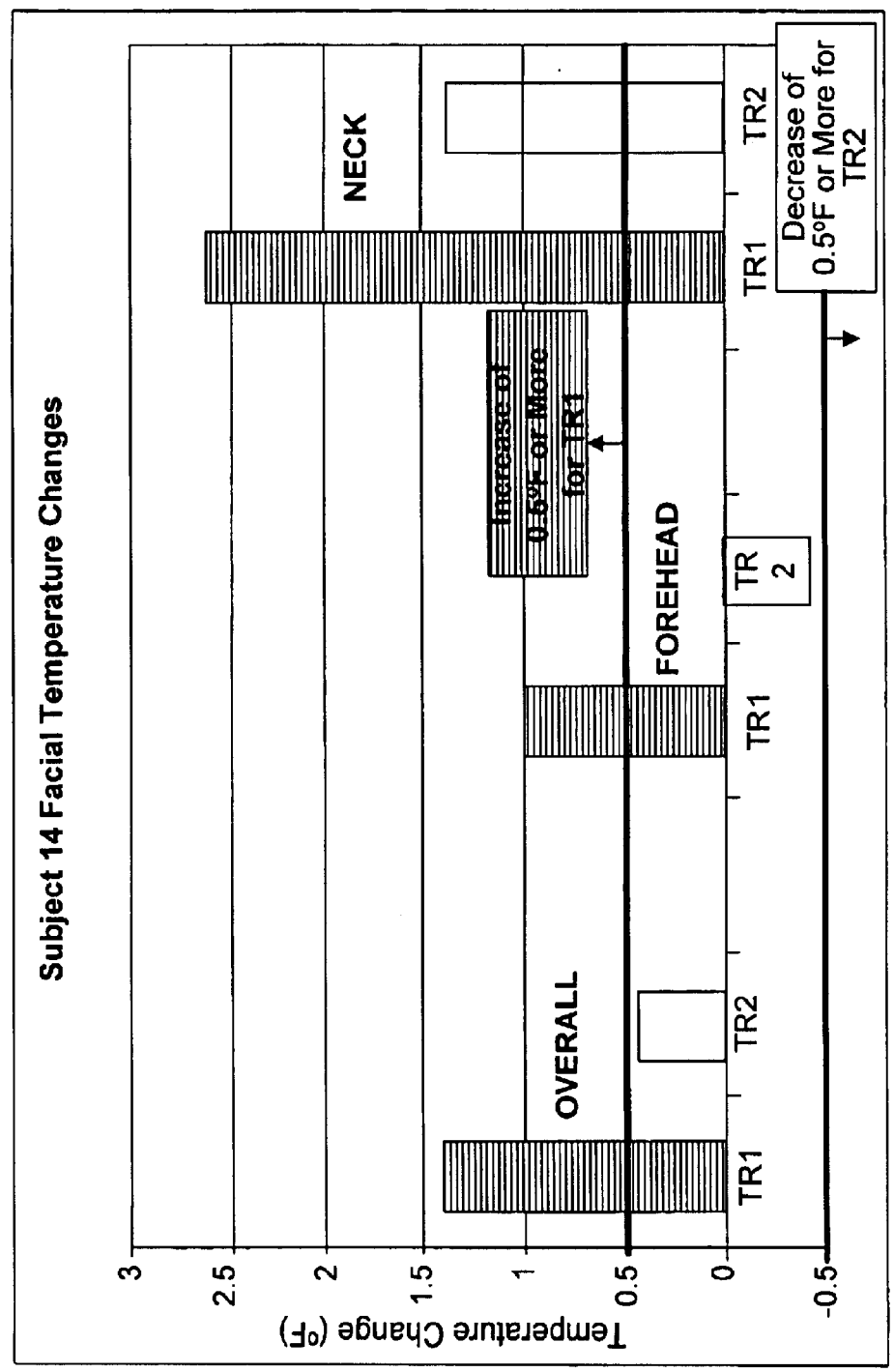
FIG. 19 is a bar graph of test results for another subject subjected to a method according to one aspect of the invention.
Figure 20:
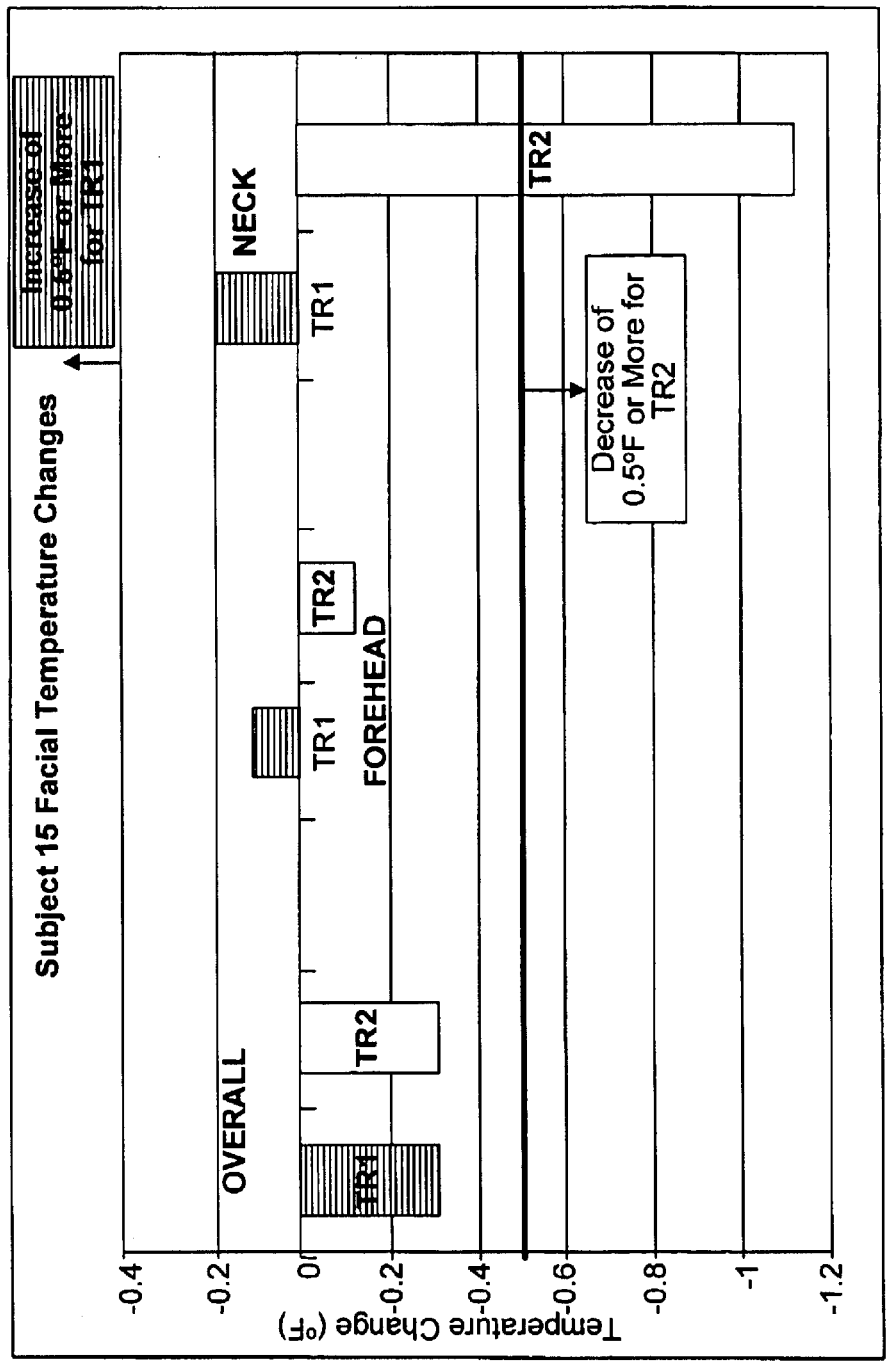
FIG. 20 is a bar graph of test results for another subject subjected to a method according to one aspect of the invention.
Figure 6:
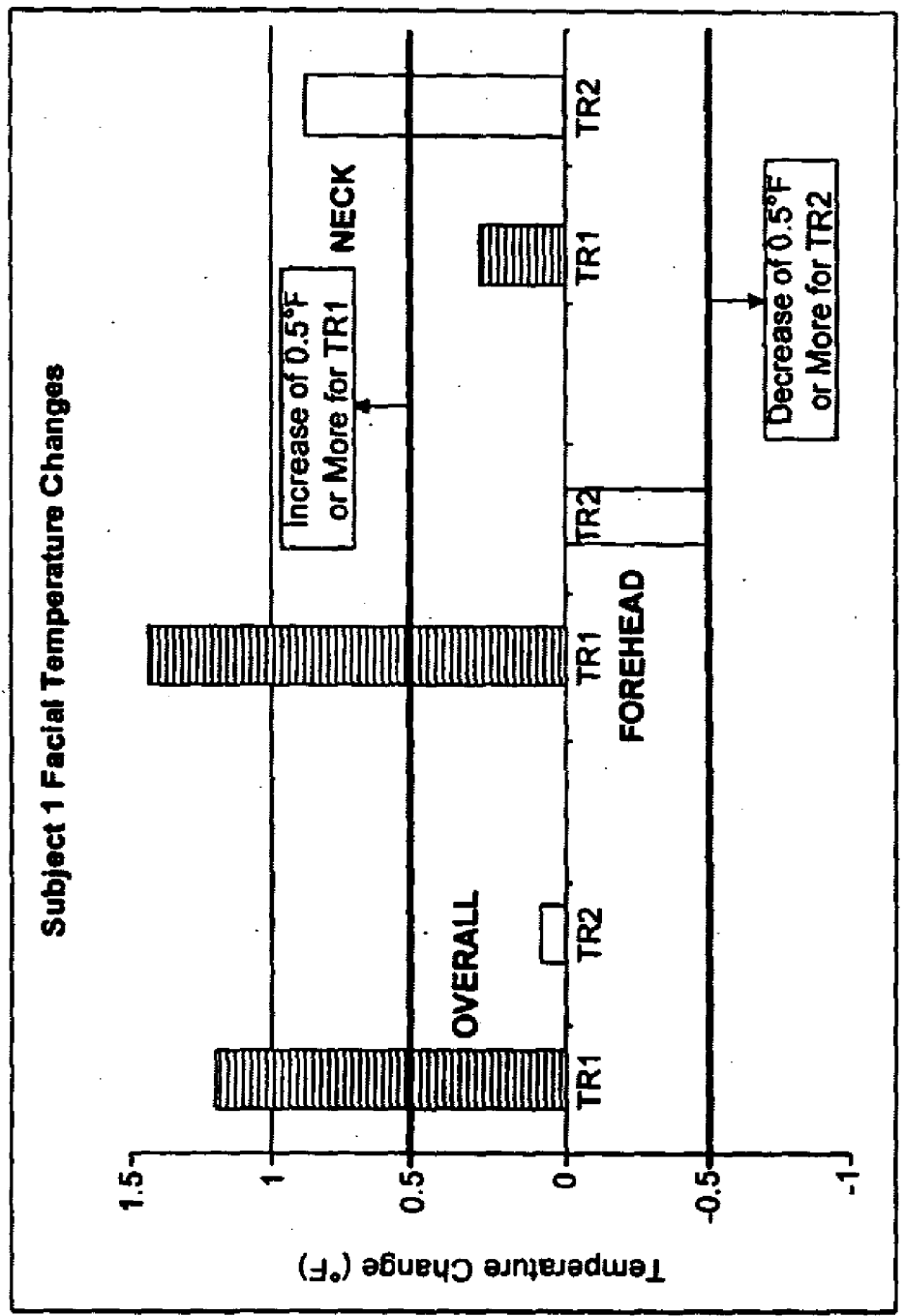
Figure 7:
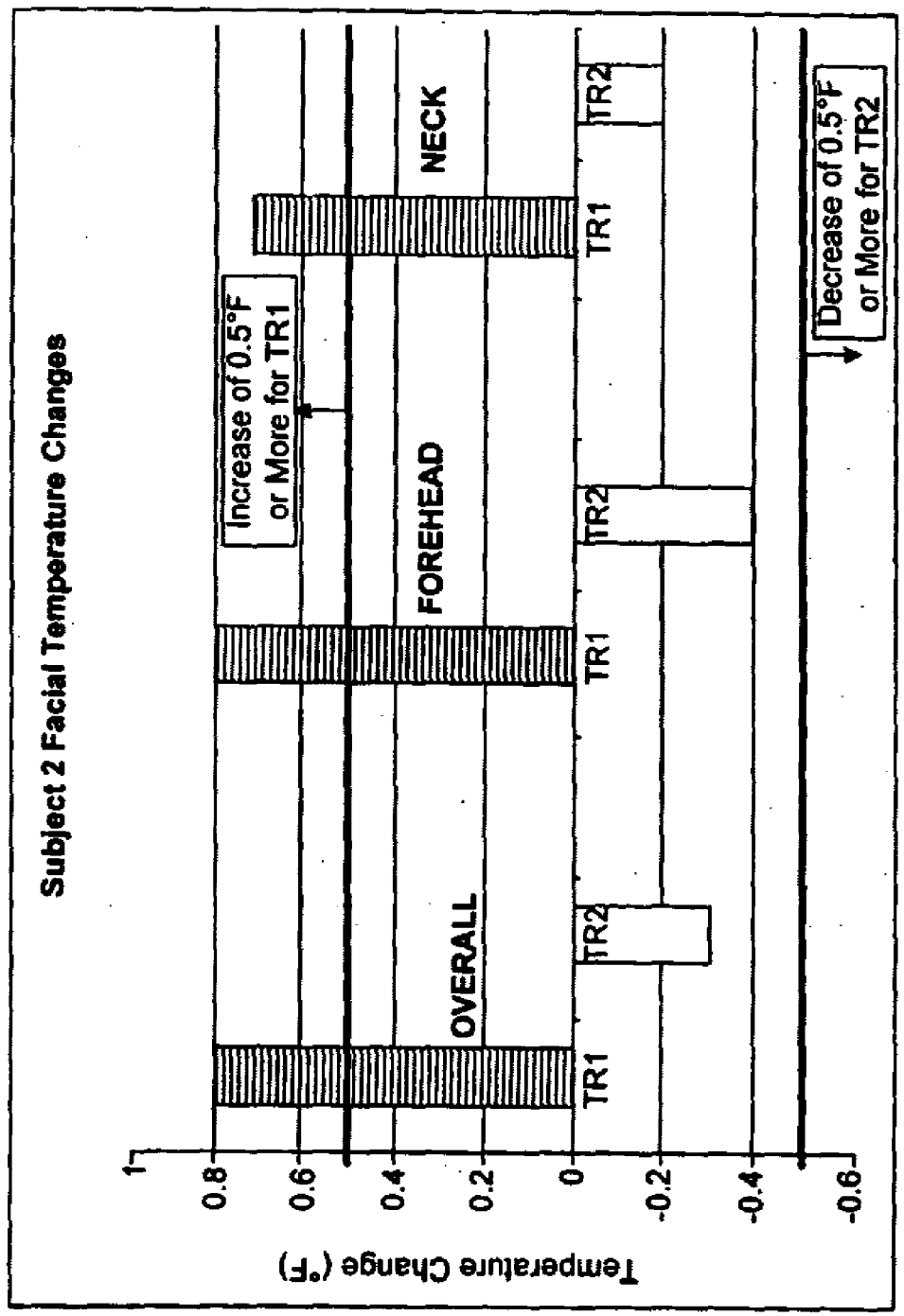
Figure 8:
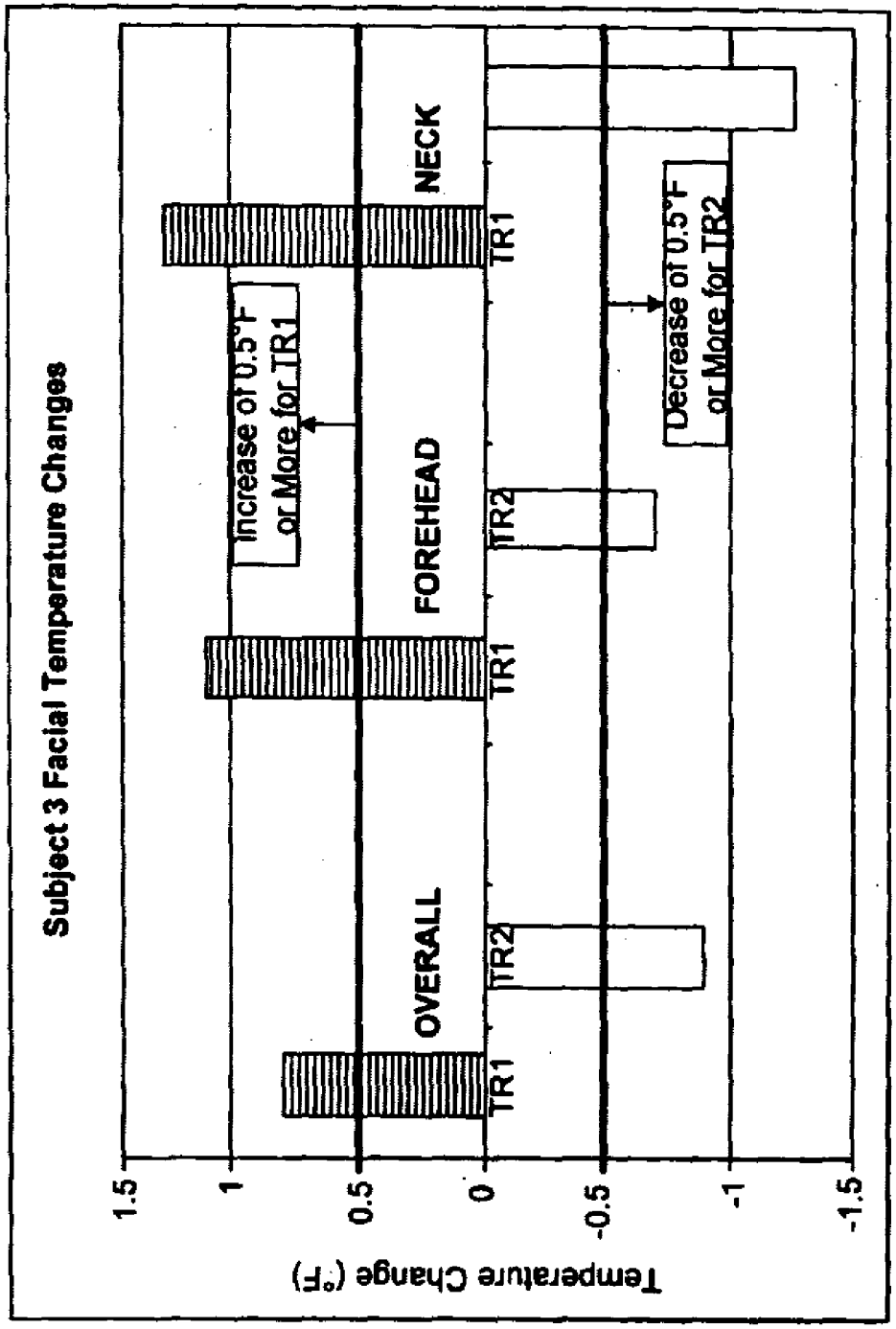
Figure 9:
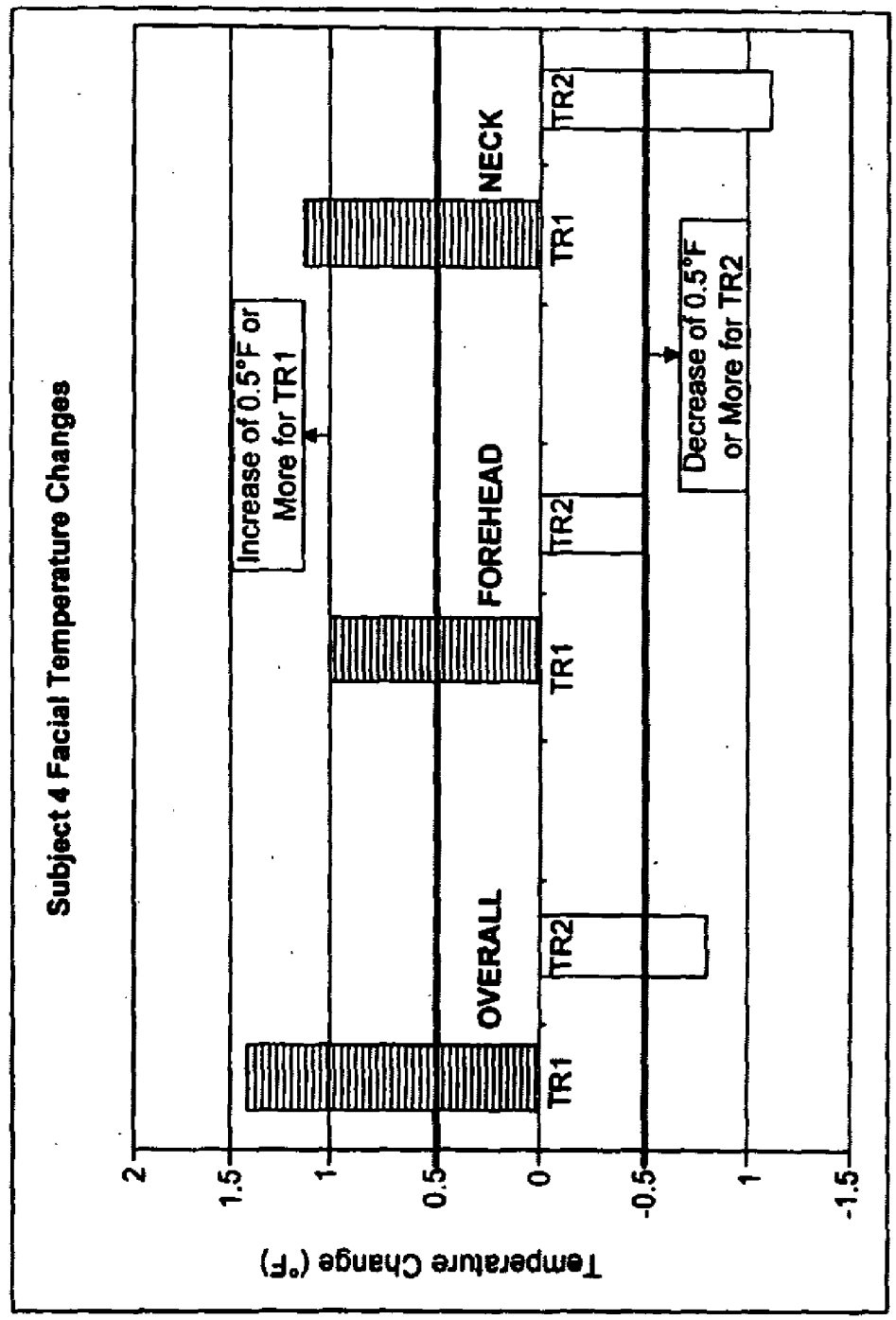
Figure 10:
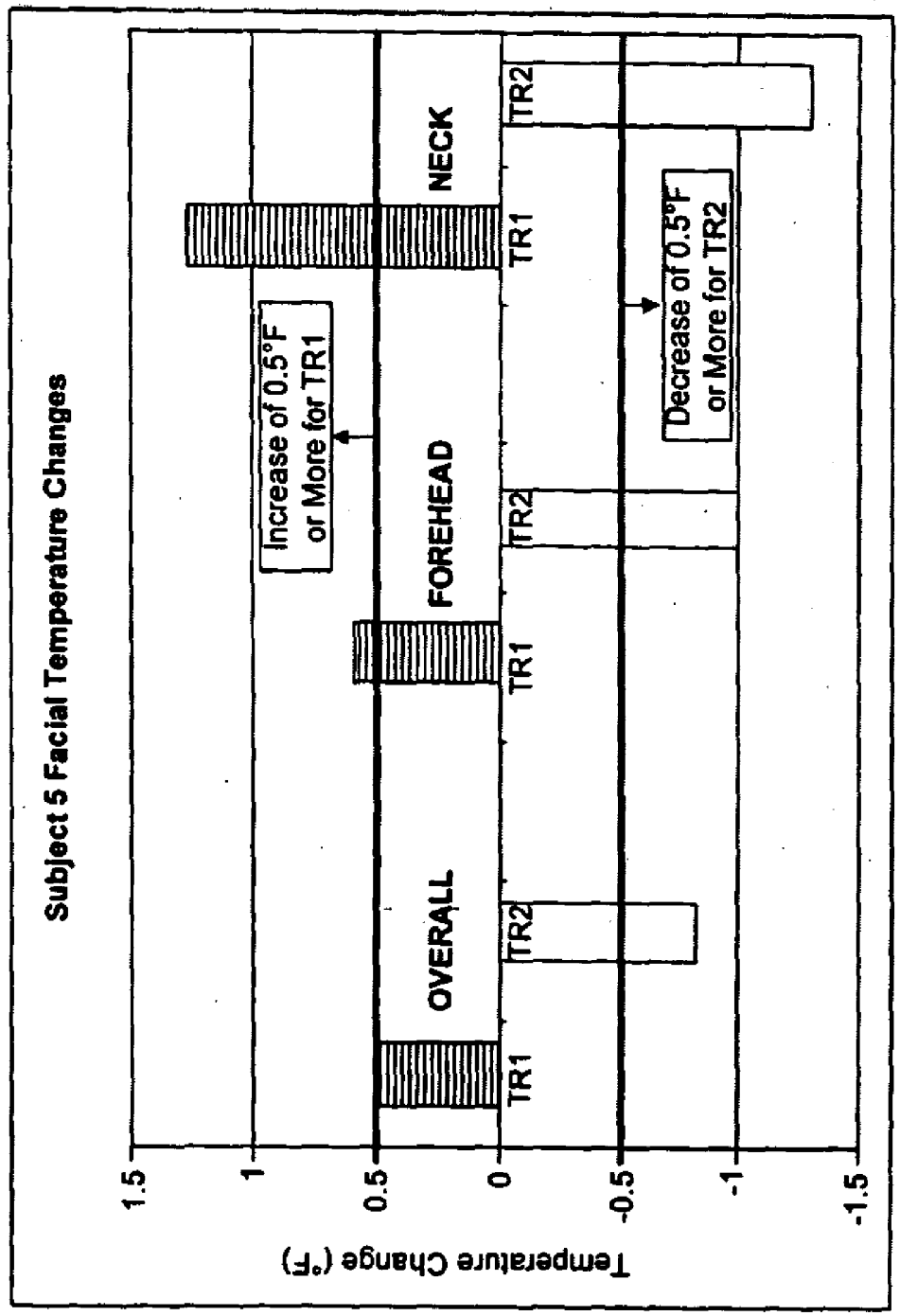
Figure 11:
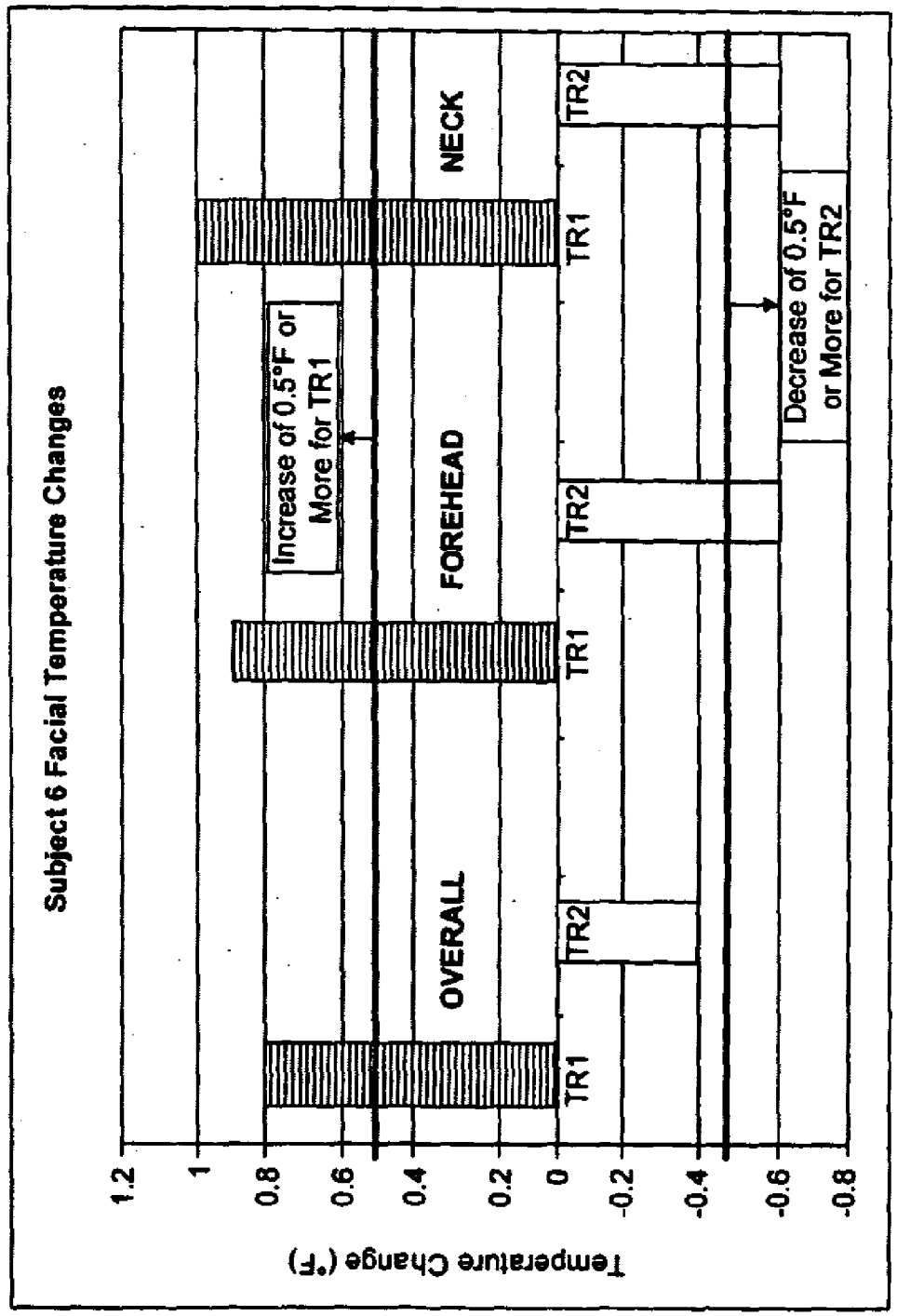
Figure 12:
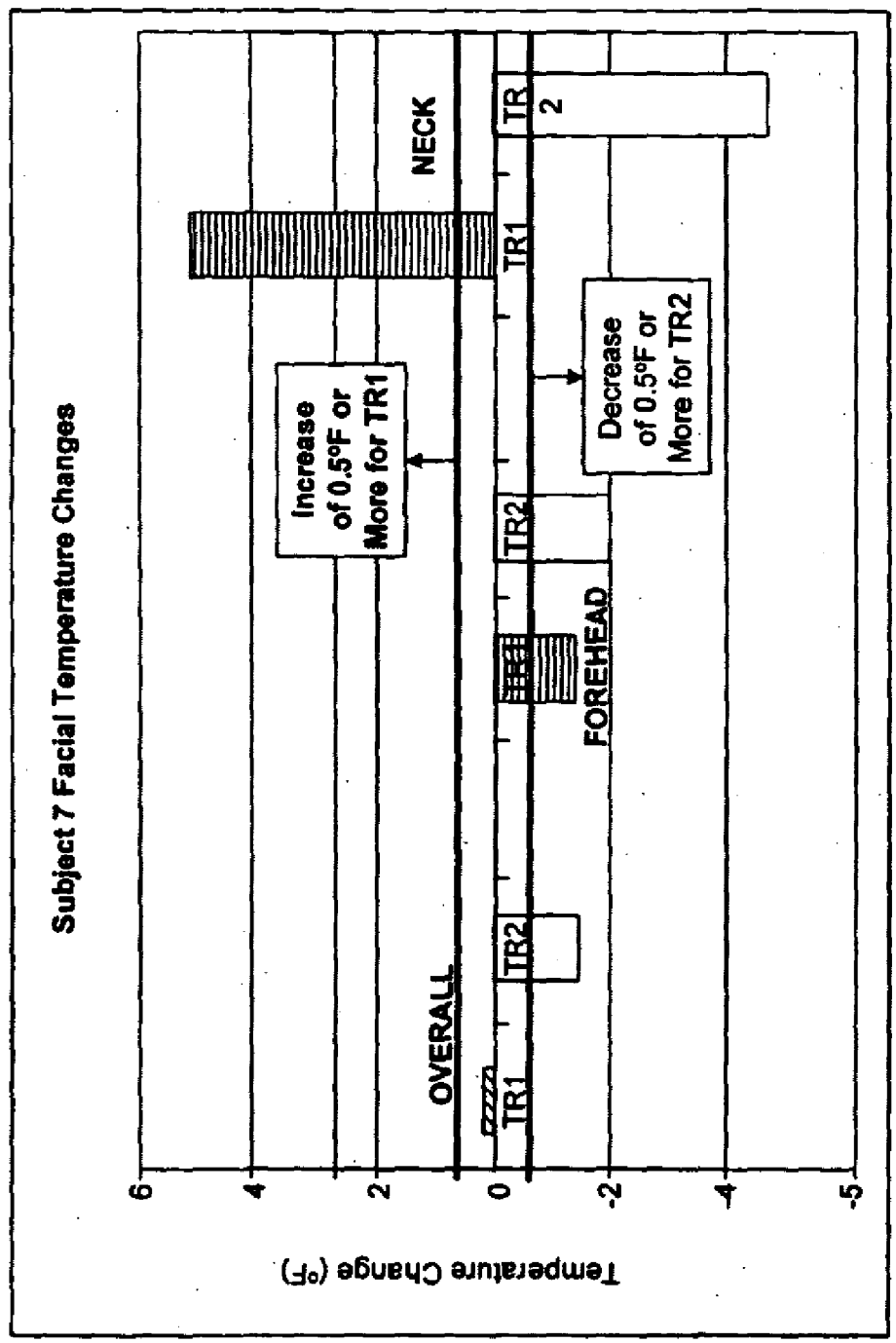
Figure 13:
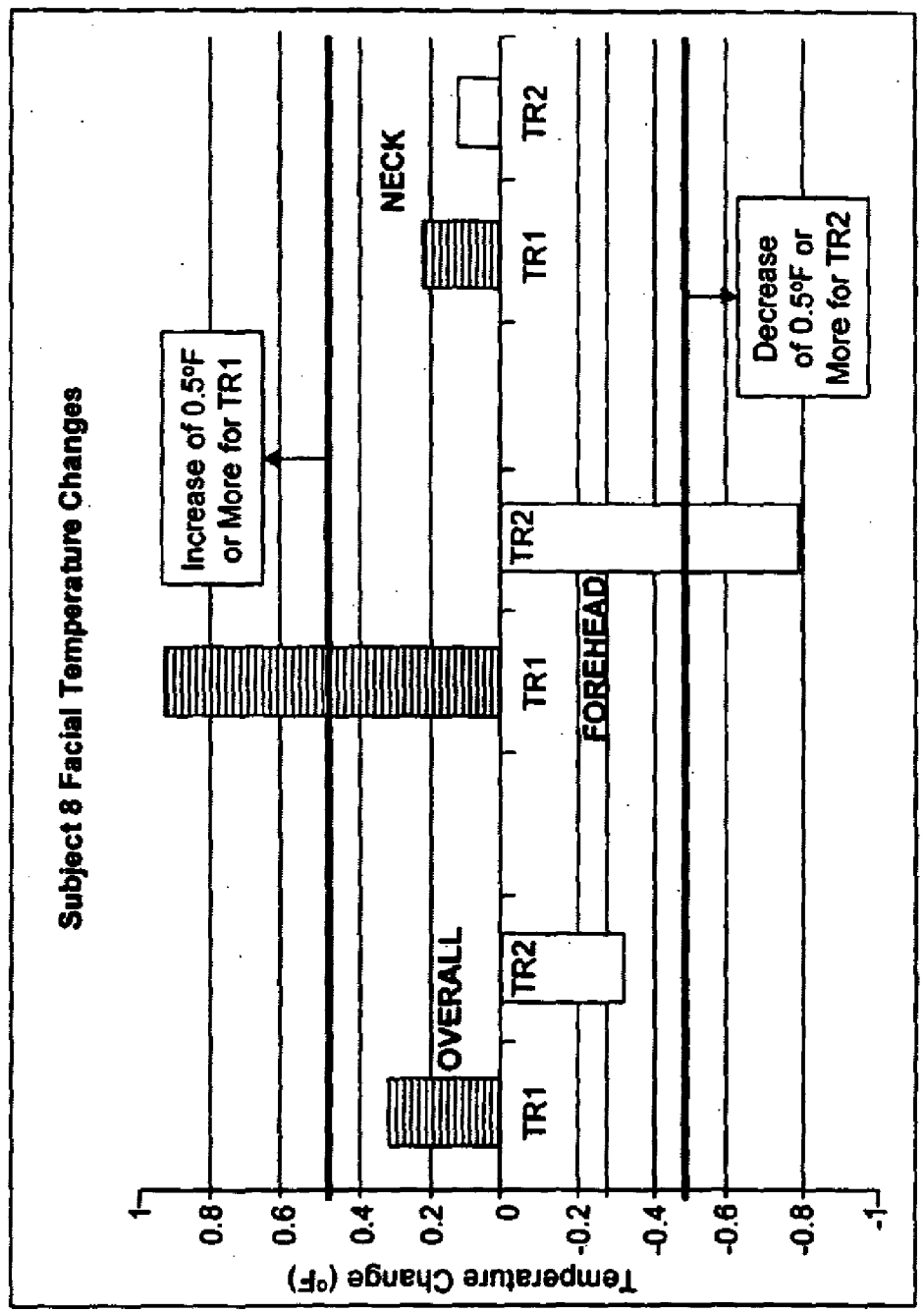
Figure 14:
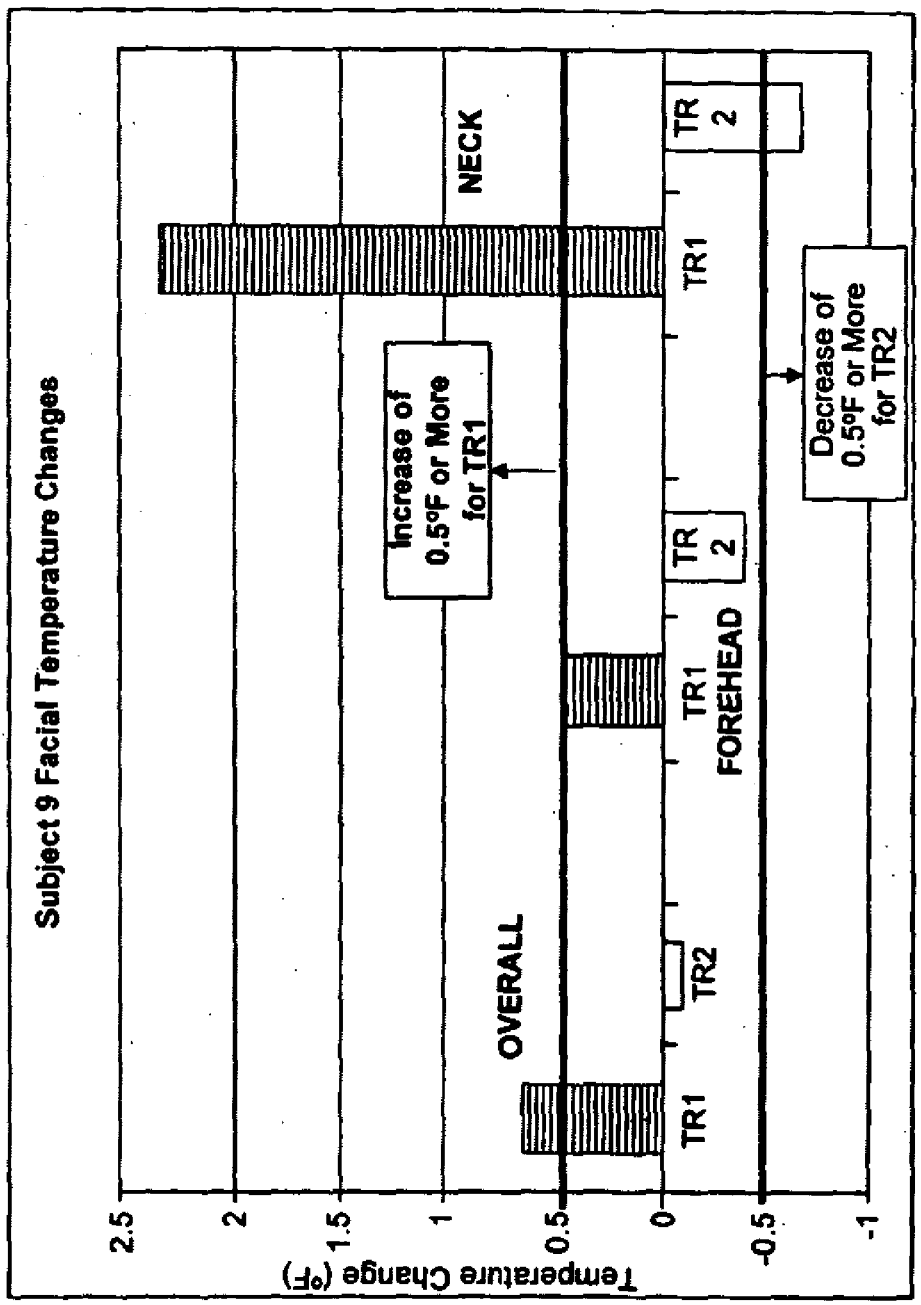
Figure 15:
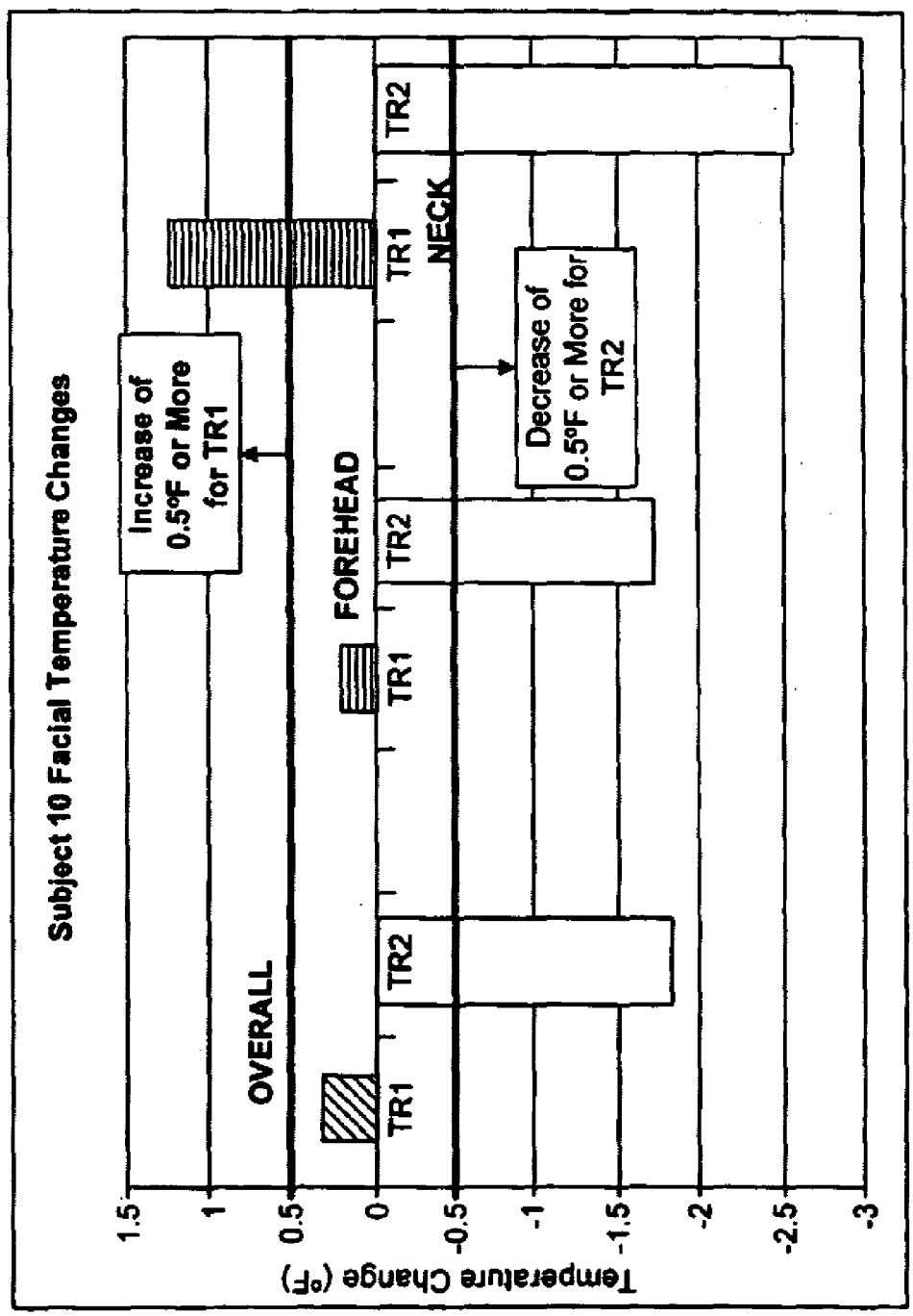
Figure 16:
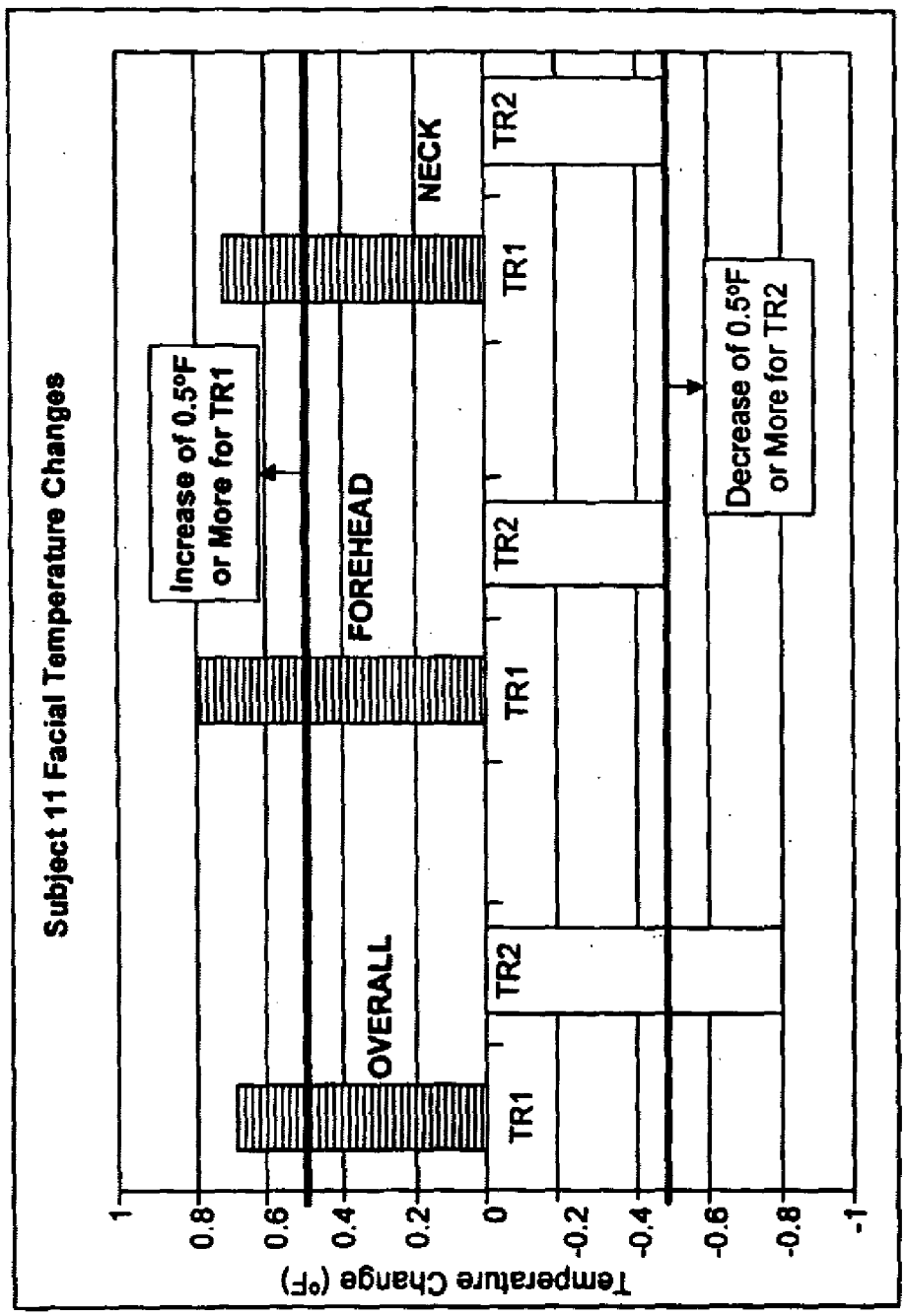
Figure 17:
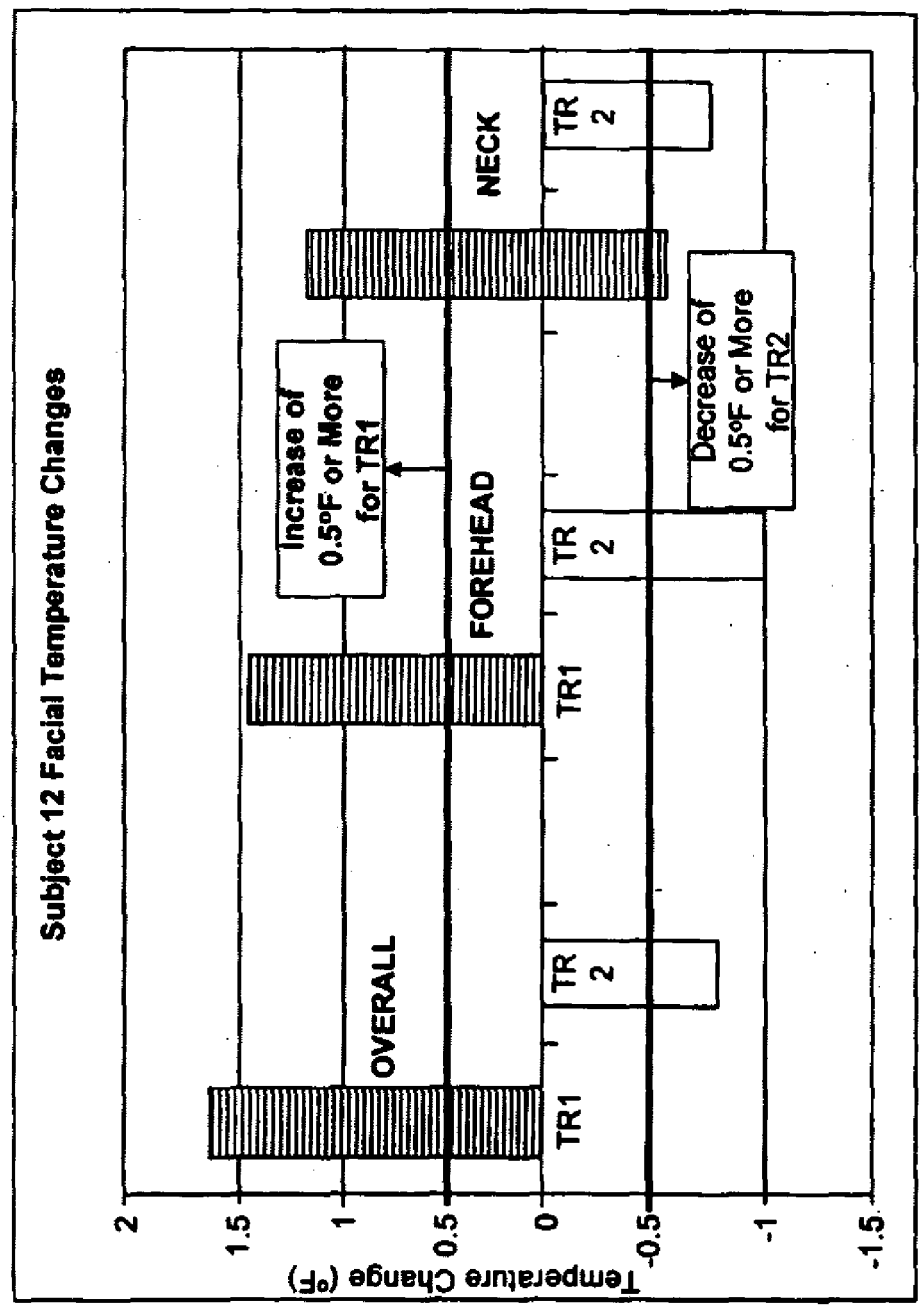
Figure 18:
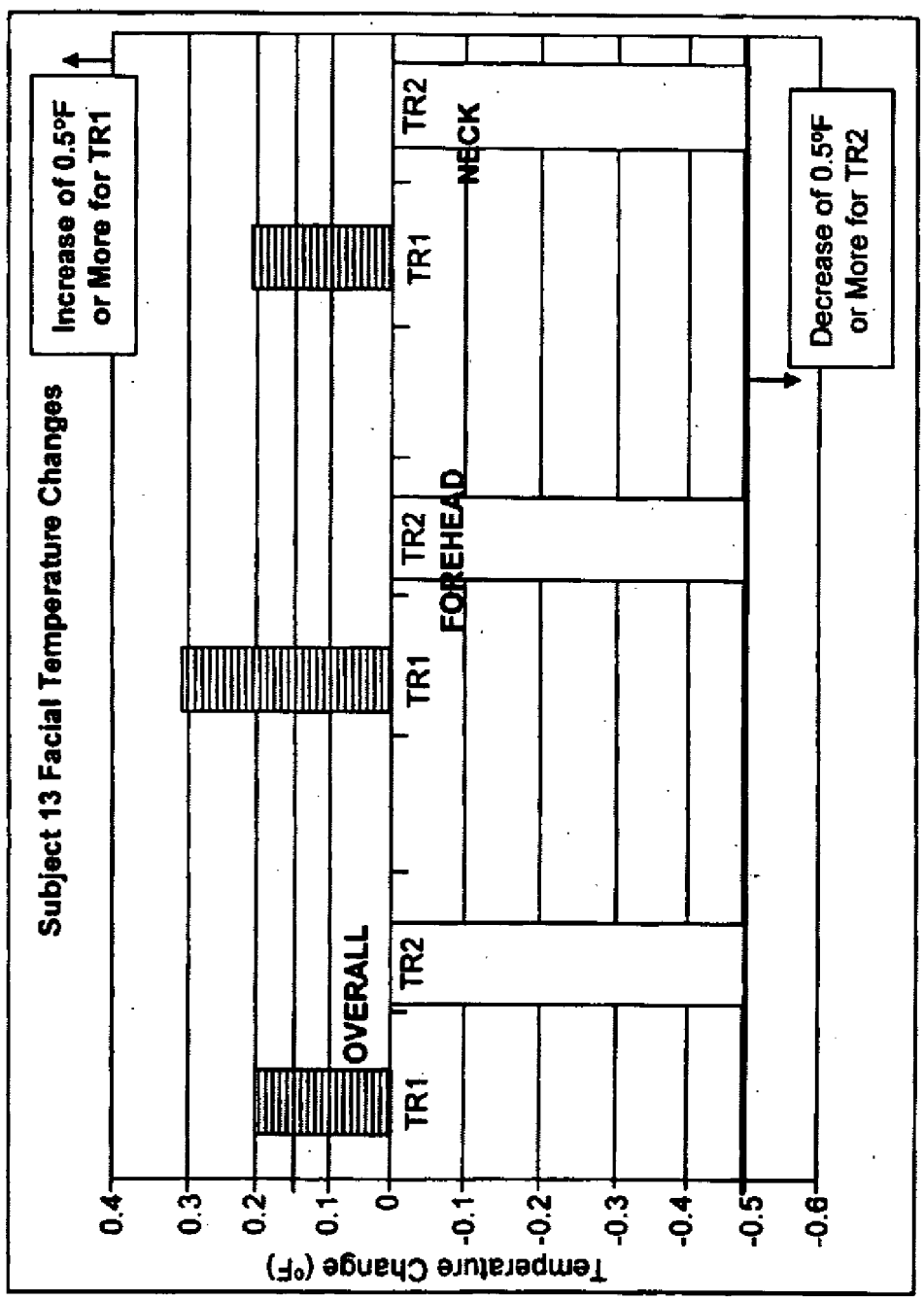
Figure 19:
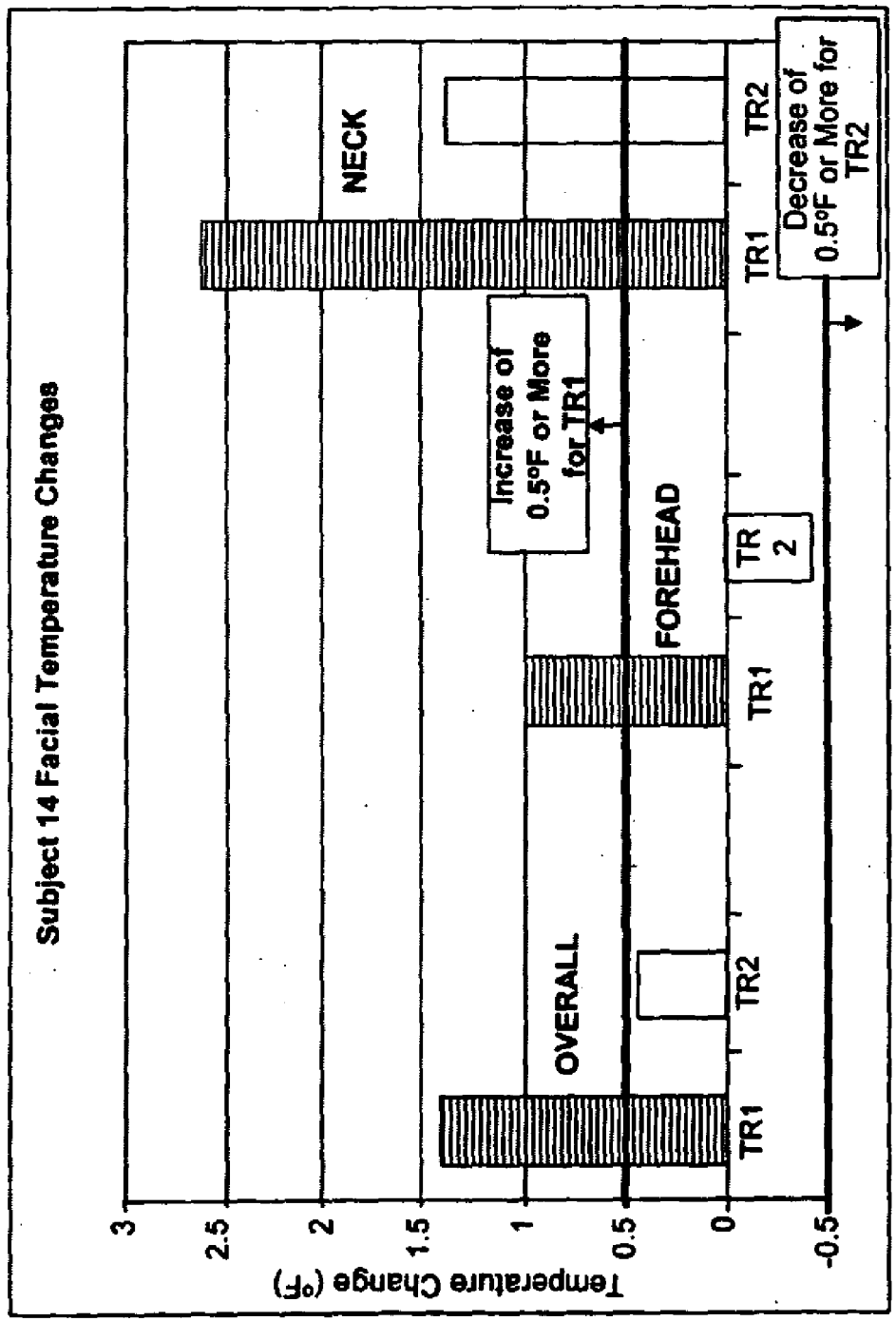
Figure 20:
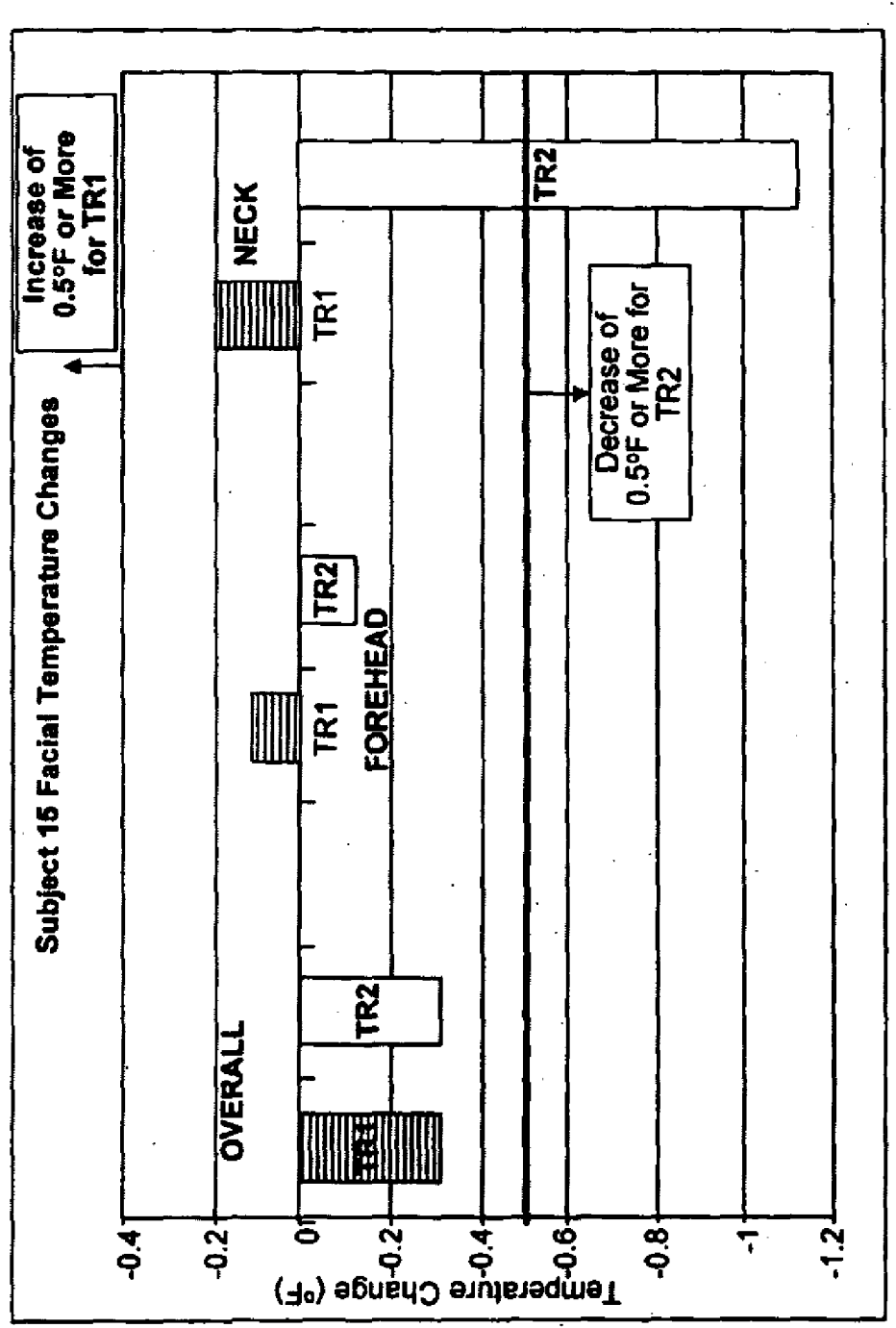

For example, the subject of FIG. 7 exhibited an increase during the first transition TR1 of nearly one degree Fahrenheit in the overall face and neck region 34 (labeled "OVERALL" in FIGS. 6-20) while exhibiting a reduction of nearly four tenths of one degree Fahrenheit during the second transition TR2 in the overall face and neck region 34. In addition, the subject of FIG. 7 also exhibited an increase of nearly one degree Fahrenheit during the first transition TR1 in the forehead region 30, and about a one half of one degree Fahrenheit temperature decrease during the second transition TR2 in the forehead region 30.

Those observable temperature changes appear to be consistent with the theory of the interaction between the SNS and the PNS described previously herein. For example, prior to the subject providing an untruthful response to the interviewer, in a relatively relaxed state, the SNS has not yet activated a "fight or flight" type response that would create an increase in temperature in the subject's skin. When the subject attempts to respond untruthfully, however, the subject may become anxious, thus activating the SNS and thereby increasing the temperature in the subject's skin. Furthermore, once the subject is no longer providing an untruthful response, the PNS counteracts the SNS and thereby reduces the temperature of the skin. Accordingly, by understanding the interaction between the lack of truthfulness of a response and the first and second transitions in the skin temperature, an observer may be able to evaluate the anxiety and/or truthfulness of a response to a request for information.

Although the subjects displayed the above-mentioned trend to exhibit the first and second transition temperature changes, the magnitude of those the temperature changes is inconsistent among the subjects. For example, the subject of FIG. 6, exhibited an increase in temperature during the second transition TR2 in the overall face and neck region 34 while all the other subjects except for the subject of FIG. 18 exhibited a decrease in the second transition TR2 in the overall face and neck region 34. A careful examination of the data, however, reveals that thirteen of the fifteen subjects exhibited a temperature change magnitude of at least one half of one degree in three of six transitions. (The six transitions include temperature changes exhibited in each of the three regions (e.g., the forehead region 30, the neck region 32, and the overall face and neck region 34) for each of the first and second transitions TR1 and TR2.) The only two subjects from the fifteen that fail to adhere to that principle are the subject of FIG. 13 and the subject of FIG. 20. As a result, the level of anxiety and/or the truthfulness of the response of a person may be evaluated by observing the magnitude of each of the six transitions that occur as a person responds to a request for information. If, for example, three of six of the transitions exceed a predetermined threshold magnitude of temperature change (e.g., one half of one degree), it may indicate that the person's response is untruthful.

In addition to manual evaluation by a requester, the data received from a device used to detect the transitions may be input into, for example, a device that is capable of automatically collecting, tabulating, and detecting changes in the transitions that reach a predetermined magnitude (such as, for example, a computer) such that the truthfulness of a person's response may be automatically evaluated. For example, a computer could be programmed to collect, tabulate, and evaluate each of any number of transitions in such a manner the that each transition provides a score based on, for example, the magnitude of the transition. The accumulated scores could be used to establish a reference score that would tend to indicate to a certain probability of whether a person's response was truthful.

It will be apparent to those skilled in the art that various modifications and variations can be made to the methodology of the present invention. Thus, it should be understood that the invention is not limited to the examples discussed in the specification. Rather, the present invention is intended to cover modifications and variations.

What is claimed is:

1. A method of measuring changes in skin temperature of a person, the method comprising:
   providing a device for measuring skin temperature;
   measuring the skin temperature of the person at at least three regions of the skin of the person;
   requesting the person to supply information;
   measuring the skin temperature at the at least three regions while the person supplies the information;
   measuring the skin temperature at the at least three regions after the person supplies the information; and
   determining the difference between the measured skin temperature of the person before the information is supplied and the measured skin temperature of the person while the information is supplied at each of the at least three regions, and the difference between the measured skin temperature of the person while the information is supplied and the measured skin temperature of the person after the information is supplied at each of the at least three regions.

2. The method of claim 1, wherein the device for measuring skin temperature comprises a thermal imaging device.

3. The method of claim 1, wherein requesting the person to supply information comprises asking the person at least one question.

4. The method of claim 1, further comprising providing a device for automatically determining the truthfulness of the person and using the device to automatically determine the truthfulness of the person based on skin temperature data supplied to the device.

5. The method of claim 1, wherein the measuring of the skin temperature of the person is unknown to the person whose skin temperature is being measured.

6. The method of claim 1, further comprising evaluating the level of anxiety of the person based on the determined differences between the measured skin temperature of the person before the information is supplied and the measured skin temperature of the person while the information is supplied, and the determined differences between the measured skin temperature of the person while the information is supplied and the measured skin temperature of the person after the information is supplied.

7. The method of claim 1, further comprising evaluating the truthfulness of the person based on the determined differences between the measured skin temperature of the person before the information is supplied and the measured skin temperature of the person while the information is supplied, and the determined differences between the measured skin temperature of the person while the information supplied and the measured skin temperature of the person after the information is supplied.

8. The method of claim 1, wherein one of the at least three regions comprises the neck of the person.

9. The method of claim 8, wherein one of the at least three regions comprises the forehead of the person.

10. The method of claim 9, wherein one of the at least three regions comprises substantially the entire face and neck of the person.

11. The method of claim 1, wherein determining the difference in skin temperature includes determining the amount of increase in skin temperature for each of the at least three regions from the skin temperature measured before the information is supplied to the skin temperature measured while the information is supplied, and determining the amount of decrease in skin temperature for each of the at least three regions from while the information is supplied to after the information is supplied.

12. The method of claim 11, wherein, if any three of the amounts of increase and decrease in skin temperature are determined to be at least a predetermined amount of change, the person is determined to be anxious.

13. The method of claim 12, wherein the predetermined amount of change is one half of one degree Fahrenheit.

14. The method of claim 11, wherein, if any three of the amounts of increase and decrease in skin temperature are determined to be at least a predetermined amount of change, the person is determined to be untruthful.

15. The method of claim 14, wherein the predetermined amount of change is one half of one degree Fahrenheit.

16. A method of increasing the security of at least one of an organization, a location, and a transportation device, the method comprising:

providing a device for measuring skin temperature;

measuring the skin temperature of the person at at least three regions of the skin of the person;

requesting the person to supply information;

measuring the skin temperature at the at least three region while the person supplies the information;

measuring the skin temperature at the at least three region after the person supplies the information; and determining the truthfulness of the person based at least partially on a combination of the difference between the measured skin temperature of the person before the information is supplied and the measured skin temperature of the person while the information is supplied at each of the at least three regions, and the difference between the measured skin temperature of the person while the information is supplied and the measured skin temperature of the person after the information is supplied at each of the at least three regions.

17. The A method of evaluating the truthfulness of a person based on information supplied by the person, the method comprising:

providing a device for measuring skin temperature;

measuring the skin temperature of the neck of the person;

requesting the person to supply information;

measuring the skin temperature of the neck of the person while the person supplies the information;

measuring the skin temperature of the neck of the person after the person supplies the information; and determining the truthfulness of the person based at least partially on a combination of the difference between the measured skin temperature of the neck of the person before the information is supplied and the measured skin temperature of the neck of the person while the information is supplied, and the difference between the measured skin temperature of the neck of the person while the information is supplied and the measured skin temperature of the neck of the person after the information is supplied.

* * * * *

UNITED STATES PATENT AND TRADEMARK OFFICE
CERTIFICATE OF CORRECTION

PATENT NO. : 6,837,615 B2
DATED : January 4, 2005
INVENTOR(S) : John Scott Newman It is certified that error appears in the above-identified patent and that said Letters Patent is hereby corrected as shown below:

Drawings,
Delete figs. 6-20 and substitute therefor the Drawing Sheets consisting of Figs. 6-20 as shown on the attached pages Column 10,
Lines 58-59, "information supplied" should read -- information is supplied --.

Column 11,
Lines 30 and 32, "region" should read -- regions --.

Column 12,
Line 11, "The A method" should read -- A method --.

Signed and Sealed this

Twenty-sixth Day of April, 2005

JON W. DUDAS
*Director of the United States Patent and Trademark Office*